(12) United States Patent
Miller et al.

(10) Patent No.: US 9,023,071 B2
(45) Date of Patent: May 5, 2015

(54) ULTRASONIC DEVICE FOR FINGERTIP CONTROL

(75) Inventors: Matthew C. Miller, Cincinnati, OH (US); Daniel W. Price, Loveland, OH (US); Cory G. Kimball, Cincinnati, OH (US); Scott A. Woodruff, Cincinnati, OH (US); William E. Clem, Bozeman, MT (US); Timothy G. Dietz, Terrace Park, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 230 days.

(21) Appl. No.: 12/557,799

(22) Filed: Sep. 11, 2009

(65) Prior Publication Data

US 2010/0069940 A1    Mar. 18, 2010

Related U.S. Application Data

(60) Provisional application No. 61/096,500, filed on Sep. 12, 2008.

(51) Int. Cl.
*A61B 17/32* (2006.01)
*A61B 17/00* (2006.01)
(Continued)

(52) U.S. Cl.
CPC .............. *A61B 17/320068* (2013.01); *A61B 2017/00017* (2013.01); *A61B 2017/00367* (2013.01);
(Continued)

(58) Field of Classification Search
CPC ............ A61B 17/320068; A61B 2017/00017; A61B 2017/00367; A61B 2017/00734; A61B 2017/00424; A61B 2017/00916; A61C 1/0015; A61C 1/07

USPC .......... 606/41, 42, 45, 79–85, 166–180, 184, 606/185, 22; 200/600, 16 D, 176, 178, 519, 200/531, 536, 547, 549, 550, 563; 338/119
See application file for complete search history.

(56) References Cited

U.S. PATENT DOCUMENTS 2,715,169 A     8/1955  High
3,968,467 A *   7/1976  Lampen et al. ............... 338/119
(Continued)

FOREIGN PATENT DOCUMENTS

DE     36 00 990       7/1987
EP     1 852 078       11/2007
(Continued)

OTHER PUBLICATIONS

International Search Report dated May 3, 2010 for Application No. PCT/US09/056616.
(Continued)

*Primary Examiner* — Kathleen Holwerda

(57) ABSTRACT

An ultrasonic surgical instrument comprises a handpiece and an ultrasonically actuated blade distal to the handpiece. The instrument includes an activation member that is operable to selectively activate the blade and a controller that is operable to select the energy level at which the blade will be activated. The activation member may comprise capacitive switches; resistive sensors; resonant cavity switching technology; infrared sensing technology; technology that uses a resonant, standing wave on a surface that is perturbed by the presence of a finger; and/or any other suitable type of technology. The controller may comprise the same. The controller may permit selection from three or more available ultrasonic energy levels. The activation member and/or controller may be manipulated from various longitudinal positions on the handpiece and/or various rotational positions about the handpiece, such that the handpiece may be gripped in a variety of ways.

10 Claims, 24 Drawing Sheets

(51) Int. Cl.
    *A61B 18/00* (2006.01)
    *A61C 1/00* (2006.01)
    *A61C 1/07* (2006.01)

(52) U.S. Cl.
    CPC .............. *A61B2017/00424* (2013.01); *A61B 2018/00916* (2013.01); *A61C 1/0015* (2013.01); *A61C 1/07* (2013.01); *A61B 2017/00734* (2013.01)

(56) References Cited

U.S. PATENT DOCUMENTS

| | | | |
|---|---|---|---|
| 4,221,975 A * | 9/1980 | Ledniczki et al. | 307/116 |
| 4,659,879 A | 4/1987 | Hasegawa | |
| 5,015,227 A | 5/1991 | Broadwin et al. | |
| 5,217,478 A * | 6/1993 | Rexroth | 606/180 |
| 5,324,299 A | 6/1994 | Davison et al. | |
| 5,555,004 A | 9/1996 | Ono et al. | |
| 5,873,873 A | 2/1999 | Smith et al. | |
| 6,258,088 B1 | 7/2001 | Tzonev et al. | |
| 6,344,619 B1 | 2/2002 | Yamasaki et al. | |
| 6,423,082 B1 | 7/2002 | Houser et al. | |
| 6,500,176 B1 | 12/2002 | Truckai et al. | |
| 6,608,263 B2 | 8/2003 | Myojin | |
| 6,666,875 B1 | 12/2003 | Sakurai et al. | |
| 6,752,816 B2 | 6/2004 | Culp et al. | |
| 6,773,444 B2 | 8/2004 | Messerly | |
| 6,945,981 B2 * | 9/2005 | Donofrio et al. | 606/169 |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,416,101 B2 | 8/2008 | Shelton, IV et al. | |
| 7,609,178 B2 * | 10/2009 | Son et al. | 341/33 |
| 7,738,971 B2 | 6/2010 | Swayze et al. | |
| 7,878,981 B2 | 2/2011 | Strother et al. | |
| 7,951,162 B2 | 5/2011 | Murphy et al. | |
| 8,047,103 B2 | 11/2011 | Davidson et al. | |
| 8,139,035 B2 * | 3/2012 | Strawn et al. | 345/173 |
| 8,172,838 B2 | 5/2012 | Schnitzler | |
| 8,419,757 B2 | 4/2013 | Smith et al. | |
| 8,461,744 B2 | 6/2013 | Wiener et al. | |
| 2004/0116952 A1 | 6/2004 | Sakurai et al. | |
| 2006/0079874 A1 | 4/2006 | Faller et al. | |
| 2007/0106158 A1 | 5/2007 | Madan et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0209990 A1 | 8/2009 | Yates et al. | |
| 2010/0069940 A1 | 3/2010 | Miller et al. | |
| 2011/0087218 A1 | 4/2011 | Boudreaux et al. | |
| 2012/0078247 A1 | 3/2012 | Worrell et al. | |
| 2012/0116367 A1 | 5/2012 | Houser et al. | |
| 2012/0116379 A1 | 5/2012 | Yates et al. | |
| 2012/0116388 A1 | 5/2012 | Houser et al. | |
| 2012/0116396 A1 | 5/2012 | Price et al. | |
| 2012/0210223 A1 | 8/2012 | Eppolito | |

FOREIGN PATENT DOCUMENTS

| | | |
|---|---|---|
| EP | 2 215 981 | 8/2010 |
| JP | 62-68447 | 3/1987 |
| JP | 2007-54665 | 3/2007 |
| JP | 2008-55151 | 3/2008 |
| WO | WO 2008/089174 | 7/2008 |

OTHER PUBLICATIONS

International Preliminary Report on Patentability dated Mar. 15, 2011 for Application No. PCT/US2009/056616.
Partial European Search Report dated Jun. 19, 2013 for Application No. EP 13160723.
Chinese Office Action dated Dec. 28, 2012 for Application No. CN 200980136024.7.
Japanese Office Action, Notification of Reasons for Refusal, dated Oct. 29, 2013 for Application No. 2011-526986.

* cited by examiner

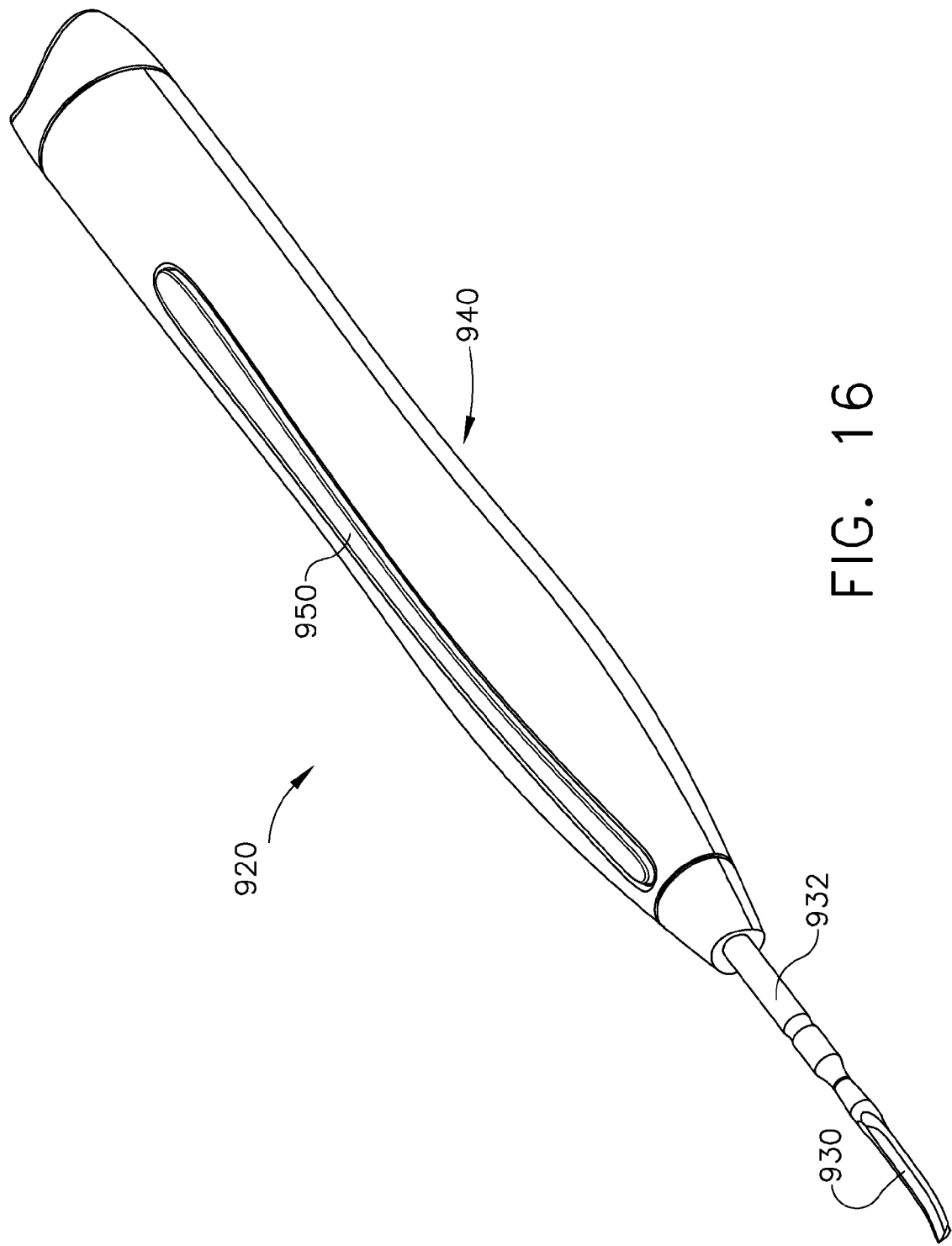

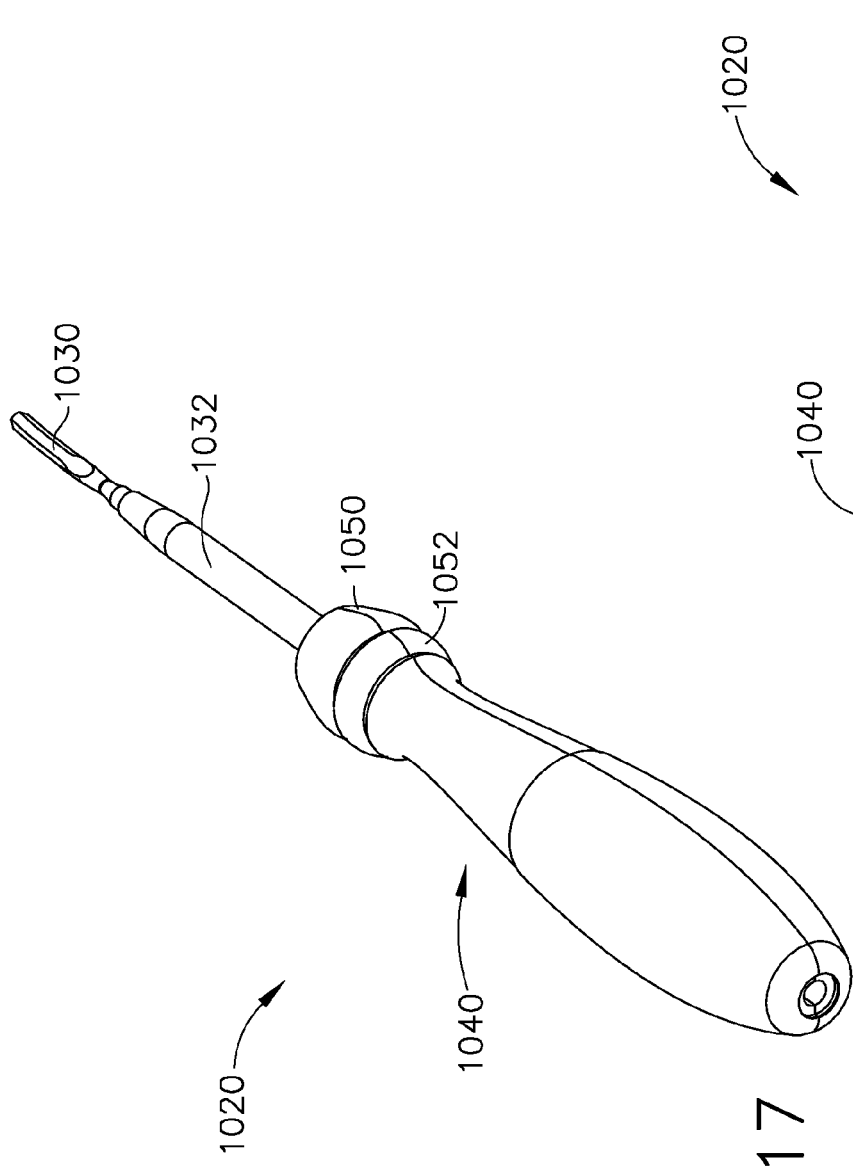
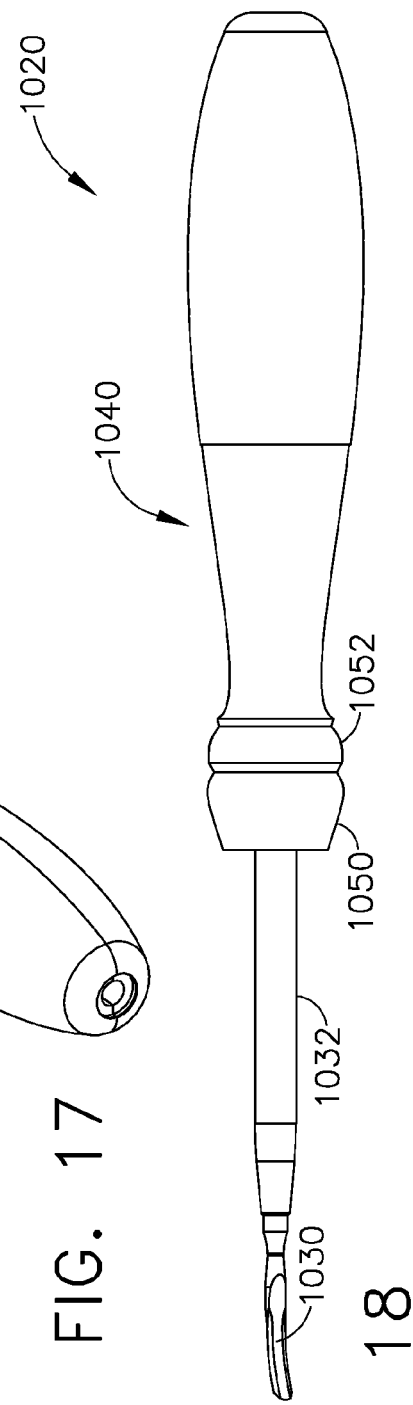
FIG. 17
FIG. 18

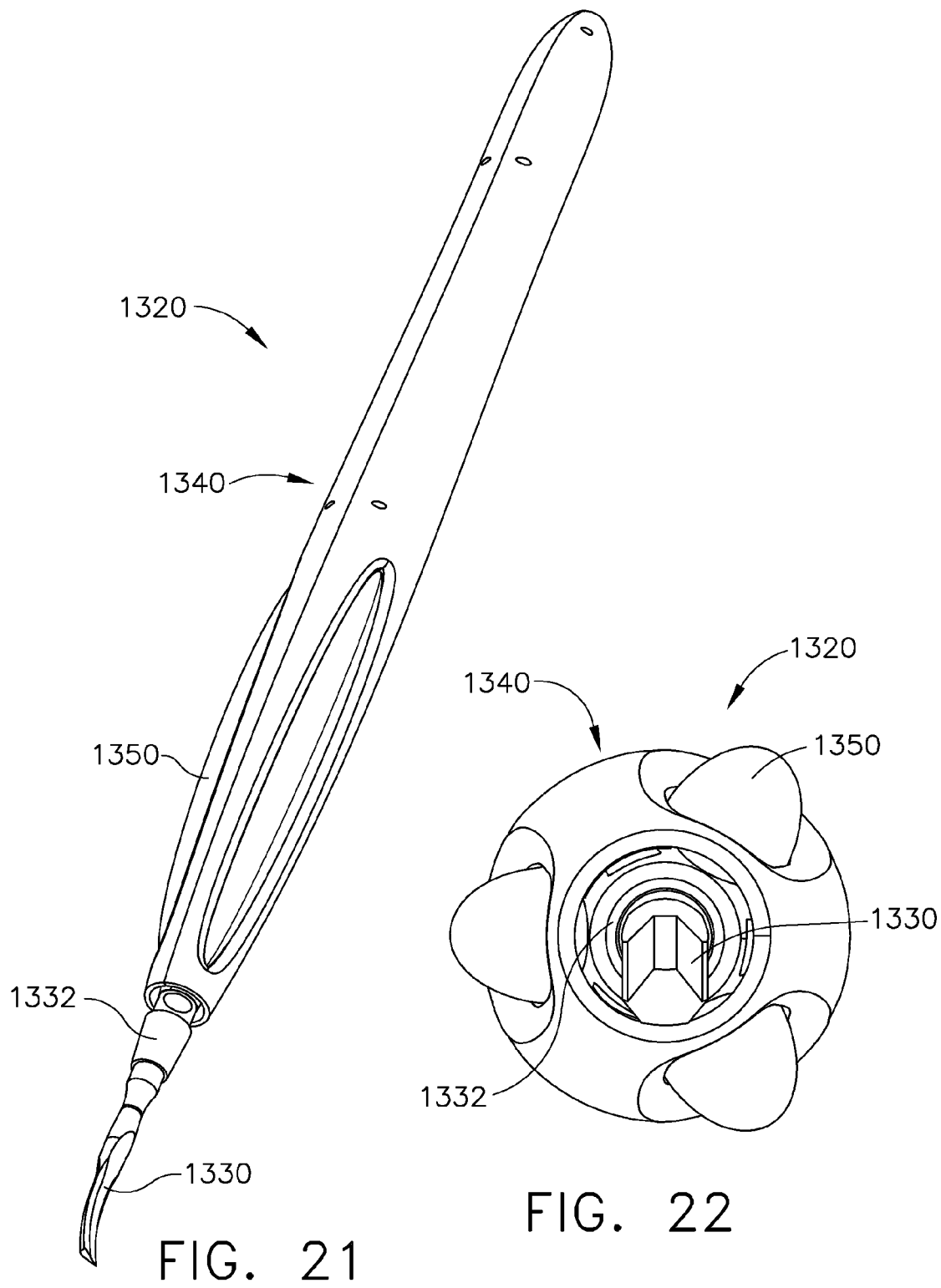

ULTRASONIC DEVICE FOR FINGERTIP CONTROL

PRIORITY

This application claims priority to U.S. Provisional Patent Application Ser. No. 61/096,500, filed Sep. 12, 2008, entitled "Ultrasonic Device for Fingertip Control," the disclosure of which is incorporated by reference herein.

BACKGROUND

Some versions of the present invention generally relate to ultrasonic surgical systems. For instance, some versions relate to an ultrasonic device that allows surgeons to perform cutting, coagulation, and/or fine dissection, such as may be required in fine and delicate surgical procedures such as plastic surgery, etc. It should be understood, however, that the teachings herein may be readily applied to various other types of devices and systems, and need not be limited to the ultrasonic surgical setting.

Ultrasonic surgical instruments may provide substantially simultaneous cutting of tissue and homeostasis by coagulation, which may minimize patient trauma. The cutting action may be realized by an end-effector, or blade tip, at the distal end of the instrument, which transmits ultrasonic energy to tissue brought into contact with the end-effector. Ultrasonic instruments of this nature can be configured for open surgical use, laparoscopic or endoscopic surgical procedures including robotic-assisted procedures, or other types of uses or procedures. Performing a plastic surgery procedure (e.g. abdominoplasty, breast reconstruction/reduction, face lift, etc.) may involve significant recovery time for the patient and risk of post-operative complications such as seroma and hematoma. The recovery time may include additional office visits post-operatively, which may affect patient satisfaction and/or decrease the amount of time a surgeon is available for surgery. In some settings, advanced energy instruments (in lieu of traditional monopolar electrosurgery—"bovie") may provide a less complicated recovery experience and potentially shorten the post-operative recovery time. However, conventional advanced energy instruments may not be suitable for plastic surgery procedures.

Some surgical instruments utilize ultrasonic energy for both precise cutting and controlled coagulation. Ultrasonic energy may cut and coagulate by using lower temperatures than those used by conventional electrosurgery. Vibrating at high frequencies (e.g., 55,500 times per second), the ultrasonic blade may denature protein in the tissue to form a sticky coagulum. Pressure exerted on tissue with the blade surface may collapse blood vessels and allow the coagulum to form a hemostatic seal. The precision of cutting and coagulation may be controlled by the surgeon's technique and adjusting the power level, blade edge, tissue traction and blade pressure, etc. Some conventional ultrasonic surgical devices may utilize a foot pedal to energize the surgical instrument. The surgeon may operate such a foot pedal to activate a generator that provides energy that is transmitted to the cutting blade for cutting and coagulating tissue while the surgeon simultaneously applies pressure to the handle to press the blade against the tissue. In some settings, the surgeon may lose focus on the surgical field while the surgeon searches for the foot pedal. The foot pedal may also get in the way of the surgeon's movement during a procedure and/or contribute to surgeon leg fatigue (e.g., during long procedures). Some uses of an ultrasonic surgical instrument may include the user using the handpiece of the instrument to apply force to tissue with the blade, even if the blade is not being ultrasonically activated (e.g., "blunt dissection").

Some conventional ultrasonic surgical devices may have finger actuation of the power at discrete locations along the length of the device. This may make it difficult to move the instrument distally and proximally to gain depth or more control. It may also require the use of a thumbwheel and/or release button to adjust the blade angle, rather than by merely rotating the wrist or rotating the entire device as if the device were a pencil. At least some conventional ultrasonic surgical devices may provide no sensory feedback to the user indicating that the end effector is energized other than momentary switch haptics. The sound created by the end effector may be above the range of human hearing and there may be no tactile vibration in the handpiece. Conventional methods of indicating the active state include an audible beep emitted by the generator. Additional, more instantaneous and local indication of activation could be achieved with visible lighting on the handpiece, audible sound feedback emanated from the handpiece, and/or haptic vibration of the handpiece.

Many types of power activation are known for various devices requiring switch control. Capacitive actuation occurs when a sensor recognizes a change in the dielectric constant of its immediate environment. A commercial example of this is the QTOUCH sensor by Atmel Corporation of San Jose, Calif. In some settings, such sensors or switches may present a risk of inadvertent activation. For instance, a capacitive switch may be inadvertently activated by fluid inadvertently spilled on the surface of the capacitive switch; or by placement of a device incorporating the capacitive switch on a surface, such that the surface activates the capacitive switch. It may therefore be desirable in certain circumstances to differentiate between intentional and unintentional activation; and/or to reduce the likelihood of (if not prevent) unintentional activation of a capacitive switch or similar switch.

One form of resistive technology is the strain gauge. The resistive properties of piezoelectric flouropolymers (PVDF) are a function of applied pressure or strain. In other words, the measured resistance is a function of applied pressure. Actuation is triggered when the applied pressure exceeds a threshold. Another form of resistive technology measures the resistance across a plane of pressure sensitive material; or utilizes the scheme developed by Transparent Products, Inc. of Valencia, Calif. A combination of resistive and capacitive sensing can be used to enhance the sensitivity and tactile feedback while reducing inadvertent activation. A capacitive sensor may require no force, only the presence of the finger to change the dielectric field. A resistive sensor may provide confirmation that a finger (e.g., rather than an accidental fluid) is the source of the dielectric change. Resonant cavity switching technology is offered by ITW ActiveTouch (a division of Illinois Tool Works Inc.) of Buffalo Grove, Ill. Other switching technology may include infrared response to the tip of the human finger to actuate. Still other switching technology may use a resonant, standing wave on a surface that is perturbed by the presence of a finger.

While a variety of ultrasonic surgical instruments have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 16 depicts a perspective view of another exemplary ultrasonic surgical device, having an elongate control and activation surface;

FIG. 17 depicts a perspective view of another exemplary ultrasonic surgical device, having a pair of activation rings;

FIG. 18 depicts an elevational view of the ultrasonic surgical device of FIG. 17;

FIG. 21 depicts a perspective view of another exemplary ultrasonic surgical device, having a plurality of control and activation surfaces;

FIG. 22 depicts an end view of the ultrasonic surgical device of FIG. 21;

Figure 1:
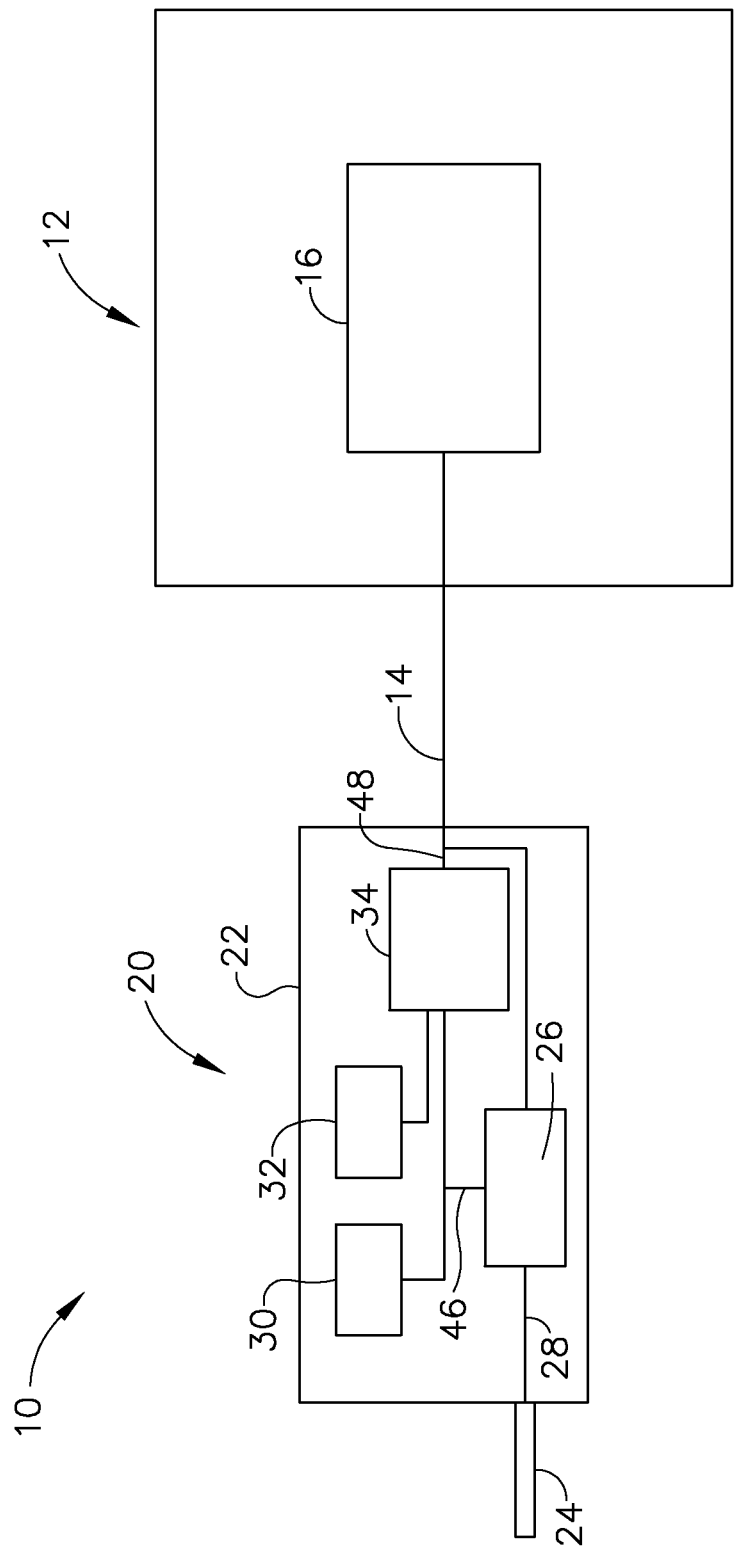
FIG. 1 depicts a block schematic view of an exemplary ultrasonic surgical system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive. Further, it is understood that any one or more of the following-described embodiments, expressions of embodiments, versions, examples, etc. can be combined with or modified in accordance with any one or more of the other following-described embodiments, expressions of embodiments, versions, examples, etc.

I. Overview

Several examples described herein are particularly directed to an improved ultrasonic surgical instrument, which is configured for effecting tissue dissecting, cutting, coagulation, and/or clamping of tissue during surgical procedures, including delicate surgical procedures, such as plastic surgery. Several examples described herein are configured for use in open surgical procedures, but may also be used in other types of surgery, including but not limited to laparoscopic surgery. Versatile use is facilitated by selective use of ultrasonic energy. When ultrasonic components of the apparatus are inactive, tissue can be manipulated, as desired, without tissue cutting or damage. When the ultrasonic components are activated, ultrasonic energy may provide for both tissue cutting and coagulation.

Further, the below examples are described in terms of a blade-only instrument. This feature is not intended to be limiting, as the examples disclosed herein may have equal application in clamp coagulator instruments as are exemplarily disclosed in U.S. Pat. Nos. 5,873,873 and 6,773,444, the disclosures of which are incorporated by reference herein.

As will become apparent from the following description, exemplary surgical instruments described herein may be particularly configured for disposable use by virtue of straightforward construction. As such, it is contemplated that the some versions of the surgical instruments be used in association with an ultrasonic generator unit of a surgical system, whereby ultrasonic energy from the generator unit provides the desired ultrasonic actuation for the surgical instrument. It will be appreciated that surgical instruments embodying the principles of the present invention may be configured for non-disposable or multiple use and/or non-detachably integrated with an associated ultrasonic generator unit.

FIG. 1 shows components of an exemplary surgical system (10) in diagrammatic block form. As shown, system (10) comprises an ultrasonic generator (12) and an ultrasonic surgical instrument (20). Generator (12) and instrument (20) are coupled together via cable (14). Cable (14) may comprise a plurality of wires, and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. By way of example only, generator (12) may comprise the GEN04 (also referred to as Generator 300) sold by Ethicon Endo-Surgery, Inc. of Cincinnati, Ohio. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of a user and manipulated by one hand (or two hands) of the user during a surgical procedure. For instance, in some versions, handpiece (22) may be grasped like a pencil by the user. In some other versions, handpiece (22) may be grasped like scissors by the user. Of course, handpiece (22) may be configured to be gripped in any other suitable fashion. A blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14), as will be described in greater detail below. By virtue of its piezoelectric properties, ultrasonic transducer (26) is operable to convert such electrical power into ultrasonic vibrational energy. By way of example only, ultrasonic transducer (26) may be constructed and operable in accordance with the teachings of U.S. Pub. No. 2007/0106158 (now U.S. Pat. No. 8,152,825), entitled "Medical Ultrasound System and Handpiece and Methods for Making and Tuning," published May 10, 2007, the disclosure of which is incorporated by reference herein. Alternatively, any other suitable ultrasonic transducer (26) may be used.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. In some versions, ultrasonic waveguide (28) may amplify the mechanical vibrations transmitted through ultrasonic waveguide (28) to blade (24). Ultrasonic transducer (26), ultrasonic waveguide (28), and blade (24) together thus form an acoustic assembly providing ultrasonic energy for surgical procedures when powered by generator (12). Handpiece (22) is configured to substantially isolate the user from the vibrations of this acoustic assembly.

Ultrasonic waveguide (28) may further have features to control the gain of the longitudinal vibration along ultrasonic waveguide (28) and/or features to tune ultrasonic waveguide (28) to the resonant frequency of the system. For instance, ultrasonic waveguide (28) may have any suitable cross-sectional dimension, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In some versions, ultrasonic waveguide (28) and blade (24) comprise product code HF105 or product code DH105, each of which is sold by Ethicon Endo-Surgery, Inc. of Cincinnati, Ohio. By way of example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). Several examples of forms that activation switch (32) may take will be described in greater detail below; while other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the user to select a desired level/amplitude of ultrasonic energy. Several examples of forms that control selector (30) may take will be described in greater detail below; while other various forms that control selector (30) may take will be apparent to those of ordinary skill in the art in view of the teachings herein. In some versions, when a user makes a selection through control selector (30), the user's selection is communicated back to control circuitry (16) of generator (12) via cable (14), and control circuitry (16) adjusts the power communicated from generator (12) accordingly. It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power having characteristics associated with the selected ultrasonic energy level/amplitude or type, via cable (14). Generator (12) may thus be operable to communicate different types or degrees of electrical power to ultrasonic transducer (26), in accordance with selections made by the user via control selector (30). In particular, and by way of example only, generator (12) may increase the voltage and/or current of the applied signal to increase the longitudinal amplitude of the acoustic structure. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein.

Figure 2:
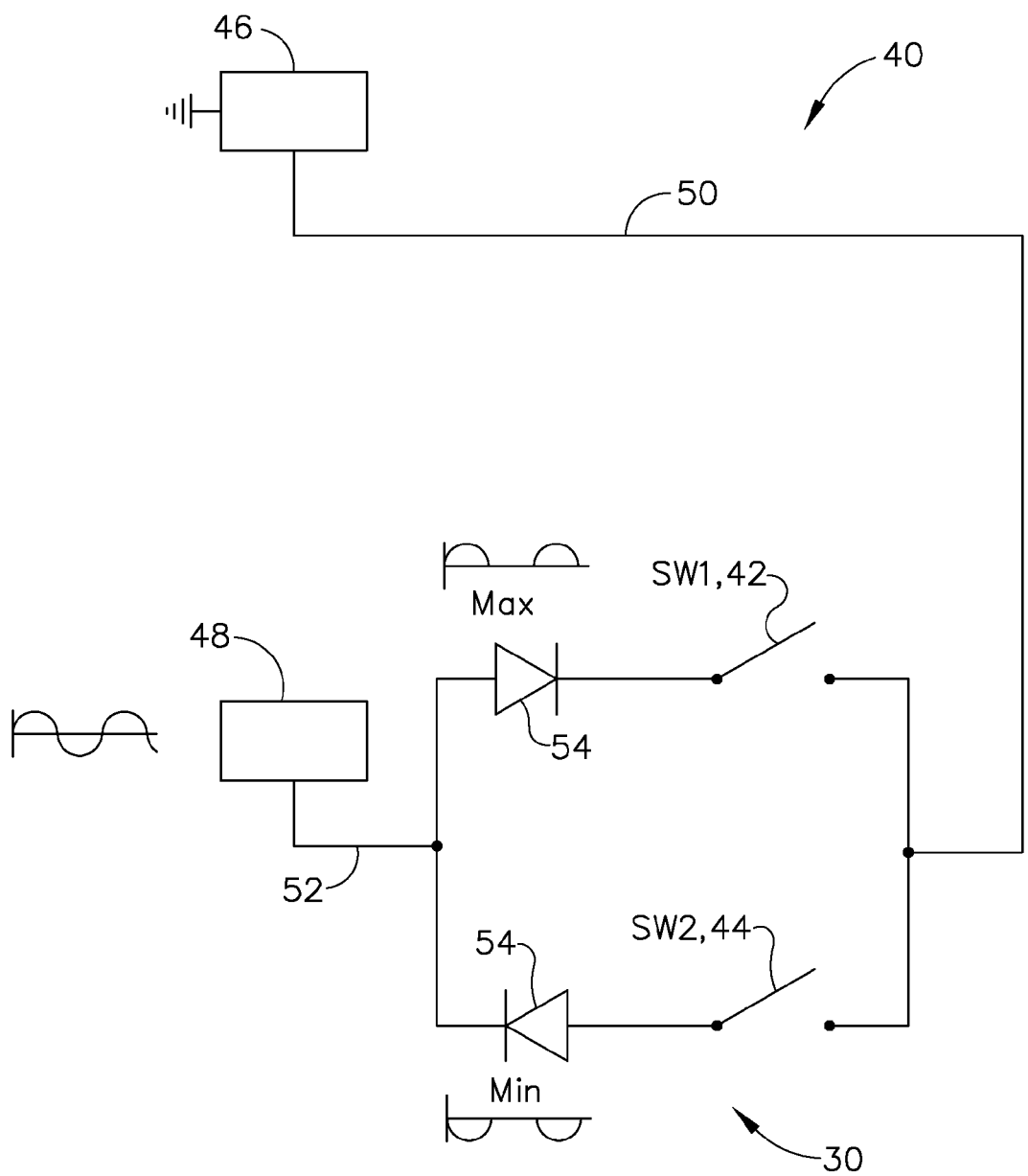
FIG. 2 depicts an electrical schematic of an exemplary hand switch circuit.

FIG. 2 depicts an exemplary circuit (40) that may be incorporated into handpiece (22) to provide selectability of ultrasonic energy for blade (24). In some versions, circuit (40) provides an electro-mechanical interface between control selector (30) and generator (12) via ultrasonic transducer (26). It should also be understood that at least a portion of circuit (40) may be incorporated into circuit board (34) in some versions. In this example, control selector (30) includes a first switch (42) that is operable to select a "maximum" level of ultrasonic energy for blade (24) and a second switch (44) that is operable to select a "minimum" level of ultrasonic energy for blade (24). While this particular example includes just two different levels of ultrasonic energy to select from, it will be apparent from the teachings below that control selector (30) may alternatively provide more than two different levels of ultrasonic energy to select from, including but not limited to a virtually infinitely variable level of ultrasonic energy within a predetermined range. It should also be understood that first and second switches (42, 44) collectively form at least part of control selector (30) in the present example. First switch (42) comprises a dome switch and second switch (44) also comprises a dome switch in this example, though any other suitable types of switches or components may be used.

Pin (48) is electrically coupled with the control signal wire from circuit board (34) to control circuitry (16) of generator (12); while pin (46) is electrically coupled with ground. Pin (46) is also coupled with control selector (30) via a conductor (50); while pin (48) is also coupled with control selector (30) via a conductor (52). In some versions, pin (46) provides a shared ground between control selector (30) and ultrasonic transducer (26). When either switch (42, 44) is activated (e.g., closed), the activated switch (42, 44) provides an electrical signal to generator (12) to activate blade (24). Circuit (40) also comprises two diodes within a diode package (54). As will be recognized by those of ordinary skill in the art, diode package (54) provides modification to a control signal communicated to generator (12), which provides modification to the electrical power received by transducer (26), which in turn provides modification to the ultrasonic action of blade (24) in accordance with the user's selections. Of course, the foregoing features and configuration of circuit (40) are merely illustrative. Circuit (40) and/or other components of handpiece (20) may otherwise be configured in accordance with the teachings of U.S. Pub. No. 2007/0191713, entitled "Ultrasonic Device for Cutting and Coagulating," published Aug. 16, 2007, the disclosure of which is incorporated by reference herein; and/or the teachings of U.S. Pub. No. 2008/0200940, entitled "Ultrasonic Energy Device for Cutting and Coagulating," published Aug. 21, 2008, the disclosure of which is incorporated by reference herein. Various other suitable features and configurations of circuit (40) will be apparent to those of ordinary skill in the art in view of the teachings herein.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the user via control selector (30), before the electrical power reaches ultrasonic transducer (26). It should be understood that in some such versions, cable (16) may be omitted entirely. In still other alternative versions, generator (12) is essentially incorporated into handpiece (22) along with all other components of surgical system (10). For instance, one or more batteries (not shown) or other portable sources of power may be provided in handpiece (22). An example of a self-contained ultrasonic surgical device is disclosed in U.S. Pat. No. 6,666,875, entitled "Surgical Apparatus Permitting Recharge of Battery-Driven Surgical Instrument in Noncontact State," issued Dec. 23, 2003, the disclosure of which is incorporated by reference herein. Still other suitable ways in which the components depicted in FIG. 1 may be rearranged or otherwise configured or modified will be apparent to those of ordinary skill in the art in view of the teachings herein.

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein.

II. Exemplary Ultrasonic Surgical Instrument with Extendable End

Figure 3:
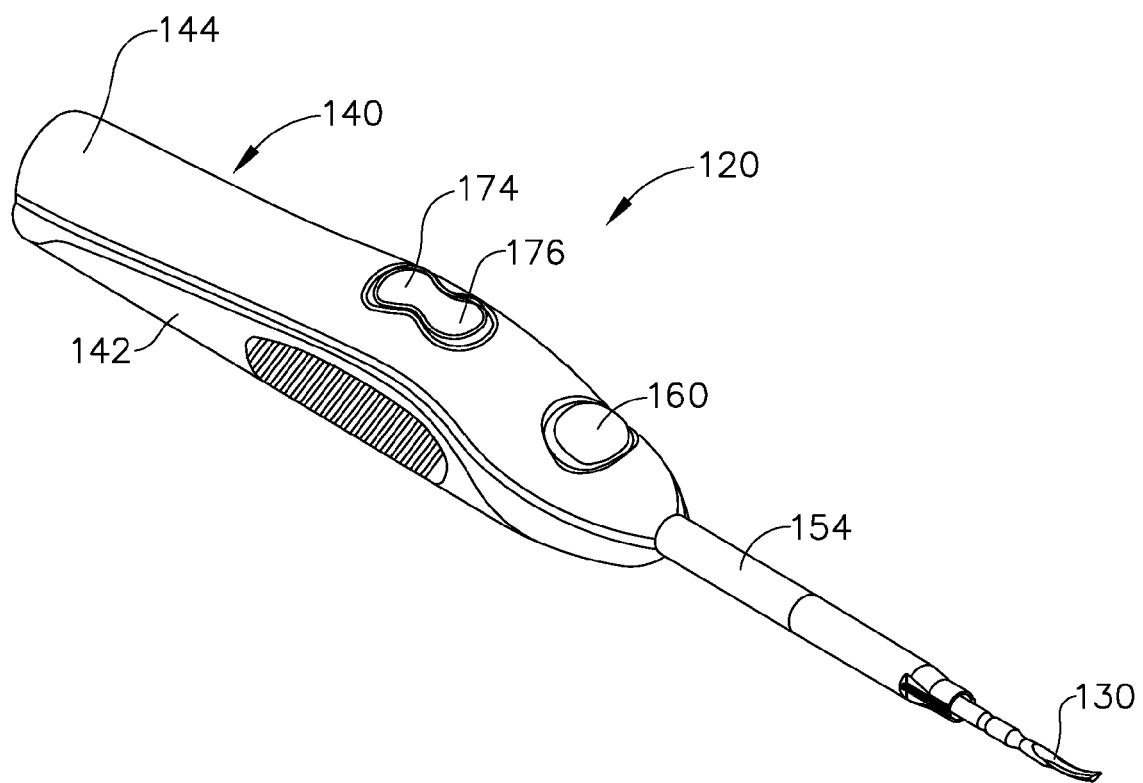
FIG. 3 depicts a perspective view of an exemplary ultrasonic surgical device.
Figure 4:
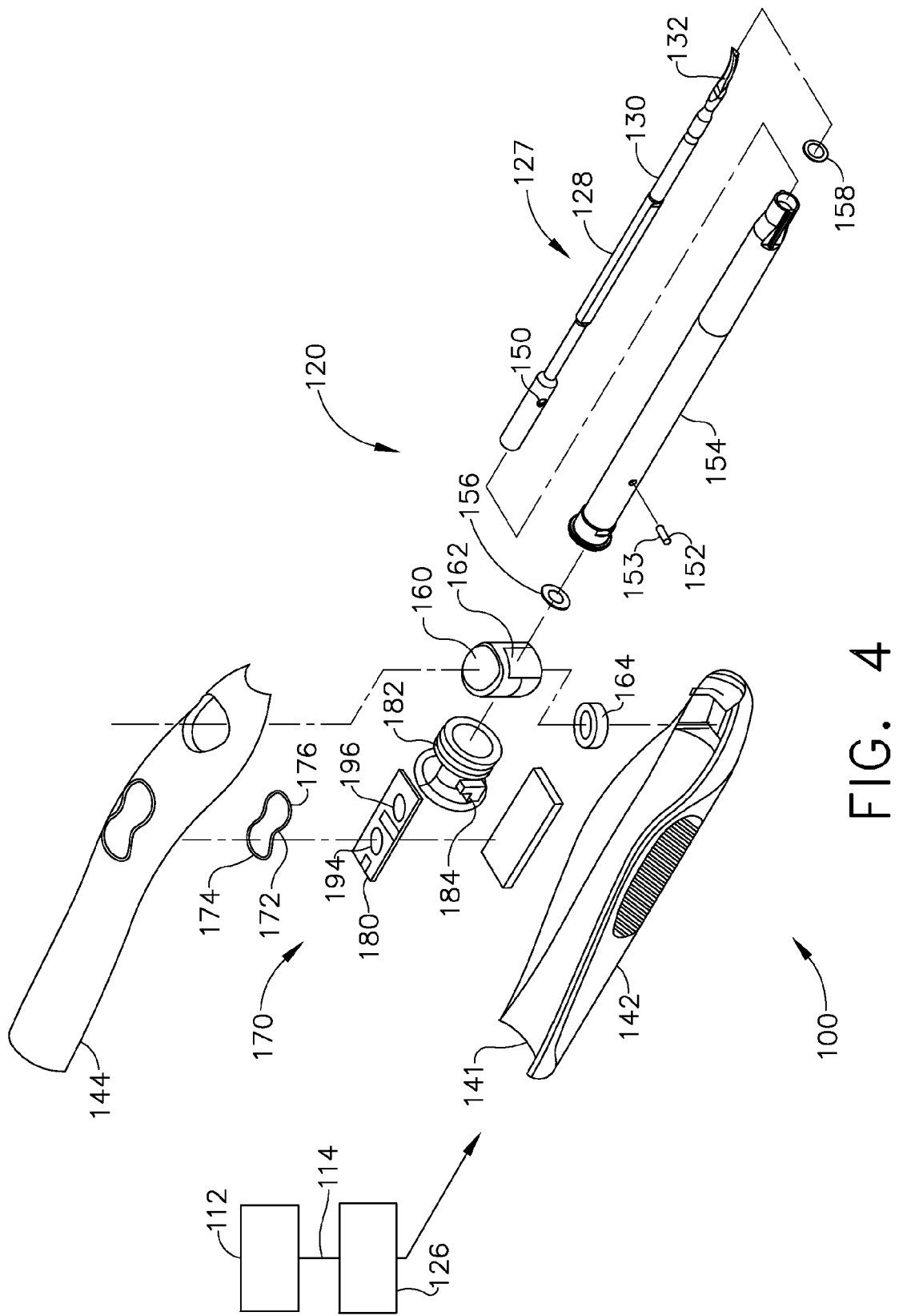
FIG. 4 depicts an exploded view of the ultrasonic surgical device of FIG. 3.

FIGS. 3-4 depict an exemplary ultrasonic surgical instrument (120), which is part of an ultrasonic surgical system (120) that includes an ultrasonic transducer (126) coupled with an ultrasonic generator (112) via a cable (114). Instrument (120) also includes an ultrasonic transmission assembly (127), which is coupled with ultrasonic transducer (126). In some versions, ultrasonic transmission assembly (127) is coupled with ultrasonic transducer (126) by a threaded connection, though any other suitable type of coupling may be used. Ultrasonic transmission assembly (127) comprises an ultrasonic waveguide (128) and blade (130). As will be apparent to those of ordinary skill in the art, when ultrasonic transducer (126) is powered by generator (112), ultrasonic transducer (126) produces ultrasonic vibrations, which are communicated to blade (130) via ultrasonic waveguide (128). This causes tip (132) of blade (130) to vibrate at an ultrasonic frequency, allowing blade (130) to be used to cut and coagulate tissue, etc.

Instrument (120) further comprises a multi-piece handle assembly (140) that is configured to substantially isolate the user from the vibrations of the acoustic assembly contained within transducer (126). By way of example only, handle assembly (140) may be shaped to be held by a user in a conventional manner, but it is contemplated that instrument (120) principally be grasped and manipulated in a pencil-like arrangement. Handle assembly (140) of the present example comprises mating housing portions (142) and (144). While a multi-piece handle assembly (140) is illustrated, handle assembly (140) may alternatively comprise a single or unitary component. Handle assembly (140) may be constructed from a durable plastic, such as polycarbonate or a liquid crystal polymer. It is also contemplated that handle assembly (140) may alternatively be made from a variety of materials or combinations of materials, including but not limited to other plastics, ceramics, and/or metals, etc. In some versions, the proximal end of instrument (120) receives and is fitted with ultrasonic transducer (126) by insertion of ultrasonic transducer (126) into handle assembly (140). Instrument (120) may be attached to and removed from ultrasonic transducer (126) as a unit. The elongated transmission assembly (127) of the instrument (120) extends orthogonally from instrument handle assembly (140).

Ultrasonic waveguide (128), which is adapted to transmit ultrasonic energy from transducer (126) to the tip (132) of blade (130), may be flexible, semi-flexible or rigid. Ultrasonic waveguide (128) may also be configured to amplify the mechanical vibrations transmitted through ultrasonic waveguide (128) to blade (130). Ultrasonic waveguide (128) may further include at least one radial hole or aperture (150) extending therethrough, substantially perpendicular to the longitudinal axis of ultrasonic waveguide (128). Aperture (150), which may be positioned at a node, is configured to receive a connector pin (152), discussed below, which connects ultrasonic waveguide (128) to an outer sheath (154). Proximal o-ring (156) and distal o-ring (158) are assembled onto transmission assembly (127) near the nodes in the present example, though various other components or configurations may be used.

Blade (130) may be integral with ultrasonic waveguide (128) and formed as a single unit. In some versions, blade (130) may be connected by a threaded connection, a welded joint, or other coupling mechanisms. The distal end of blade (130), or blade tip (132), is disposed near an anti-node in order to tune the acoustic assembly to a preferred resonant frequency $f_0$ when the acoustic assembly is not loaded by tissue. When ultrasonic transducer (126) is energized, blade tip (132) is configured to move substantially longitudinally (along the x axis) in the range of, for example, approximately 10 to 500 microns peak-to-peak, and perhaps in the range of about 20 to about 200 microns, at a predetermined vibrational frequency $f_0$ of, for example, 55,500 Hz. Blade tip (132) may also vibrate in the y-axis at about 1 to about 10 percent of the motion in the x-axis. Of course, movement of blade tip (132) may alternatively have any other suitable characteristics.

Ultrasonic waveguide (128) is positioned within outer sheath (154) and held in place via pin (152). Pin (152) may be made of any compatible metal, such as stainless steel or titanium or a durable plastic, such as polycarbonate or a liquid crystal polymer. Alternatively, any other suitable material or combination of materials may be used. In some versions, pin (152) is partially coated with an elastomeric material, such as silicon, etc., for that portion (153) of pin (152) that extends through ultrasonic waveguide (128). Elastomeric material may provide insulation from the vibrating blade throughout the length of hole (152). In some settings, this may enable high efficiency operation whereby minimal overheating is generated and maximum ultrasonic output power is available at blade tip (132) for cutting and coagulation, etc. Of course, such elastomeric material is merely optional.

Outer sheath (154) passes through an aperture (162) of release button (160). Positioned below release button (160) and within housing portion (142) is a spring (164) that asserts an upward force on release button (160). The upward force causes the perimeter of aperture (162) to firmly assert pressure against outer sheath (154), and thereby selectively prevents outer sheath (154), ultrasonic waveguide (128), and blade (130) from either rotating within handle (140) or axially translating with respect to handle (140). When the user exerts a downward force on release button (160), spring (164) is compressed and it no longer asserts a holding force on outer sheath (154). The user may then axially translate outer sheath (154), ultrasonic waveguide (128), and blade (130) relative to handle (140) and/or rotate outer sheath (154), ultrasonic waveguide (128), and blade (130) relative to handle (140). Accordingly, it should be understood that the longitudinal and/or rotational position of blade (130) relative to handle (140) may be selectively changed by the user, while still allowing blade (130) to vibrate ultrasonically at such selected positions, allowing blade (130) to be used in various surgical procedures at such selected positions. To initiate such ultrasonic action of blade (130), the user may operate a footswitch (not shown), activate a pushbutton (174, 176) as described below, activate a button on generator (112), or perform some other act on some component of system (100).

In the present example, housing of handle (140) includes a proximal end, a distal end, and a cavity (141) extending longitudinally therein. Cavity (141) is configured to accept a switch assembly (170) and ultrasonic transducer assembly (126). In one some versions, the distal end of ultrasonic transducer assembly (126) threadedly attaches to the proximal end of ultrasonic waveguide (128), though any other suitable type of coupling may be used. The distal end of ultrasonic transducer (126) also interfaces with switch assembly (170) to provide the surgeon with finger-activated controls on surgical instrument (120). Ultrasonic transducer (126) of the present example includes two conductive rings (not shown) which are securely disposed within the body of ultrasonic transducer (126) as is described in U.S. Pub. No. 2007/0106158 (now U.S. Pat. No. 8,152,825), entitled "Medical Ultrasound System and Handpiece and Methods for Making and Tuning," published May 10, 2007, the disclosure of which is incorporated by reference herein. Switch assembly (170) of the present example comprises a pushbutton assembly (172), a circuit assembly (180), a switch housing (182), a first pin conductor (184), and a second pin conductor (not shown). Switch housing (182) is annular-shaped and is supported within handle assembly (140) by way of corresponding supporting mounts on switch housing (182) and housing portions (142, 144).

Pushbutton assembly (172) of the present example comprises pushbuttons (174, 176). Circuit assembly (180) provides for the electro-mechanical interface between pushbuttons (174, 176) and generator (112) via ultrasonic transducer (126). Circuit assembly (180) comprises two dome switches (194, 196) that are mechanically actuated by depressing pushbuttons (174, 176) respectively. Dome switches (194, 196) are electrical contact switches, that when depressed provide an electrical signal to generator (112). Pins (not shown) are electrically connected to dome switches (194, 196). In particular, one end of each pin is electrically connected to a corresponding dome switch (194, 196). The other end of each pin is electrically connected with a corresponding ring conductor at the distal end of ultrasonic transducer (126). That is, the pins each have spring-loaded tips that interface with ultrasonic transducer (126) in a manner similar to that described above. Circuit assembly (180) also comprises two diodes within a diode package (not shown) that connect to the pins, respectively. While the pins provide electrical contact to the ring conductors of ultrasonic transducer, the ring conductors are in turn connected to conductors in cable (114) that connects to generator (112). Of course a variety of alternative configurations may be used.

As is readily apparent, by depressing pushbuttons (174, 176) the corresponding contact surfaces depress against corresponding dome switches (194, 196) to selectively activate the circuit (180). For instance, when the surgeon depresses pushbutton (174), generator (112) may respond with a certain energy level, such as a maximum ("max") power setting. When the surgeon depresses pushbutton (176), generator (112) may respond with a certain energy level, such as a minimum ("min") power setting, which conforms to accepted industry practice for pushbutton location and the corresponding power setting. Instrument (120) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability.

Figure 5:
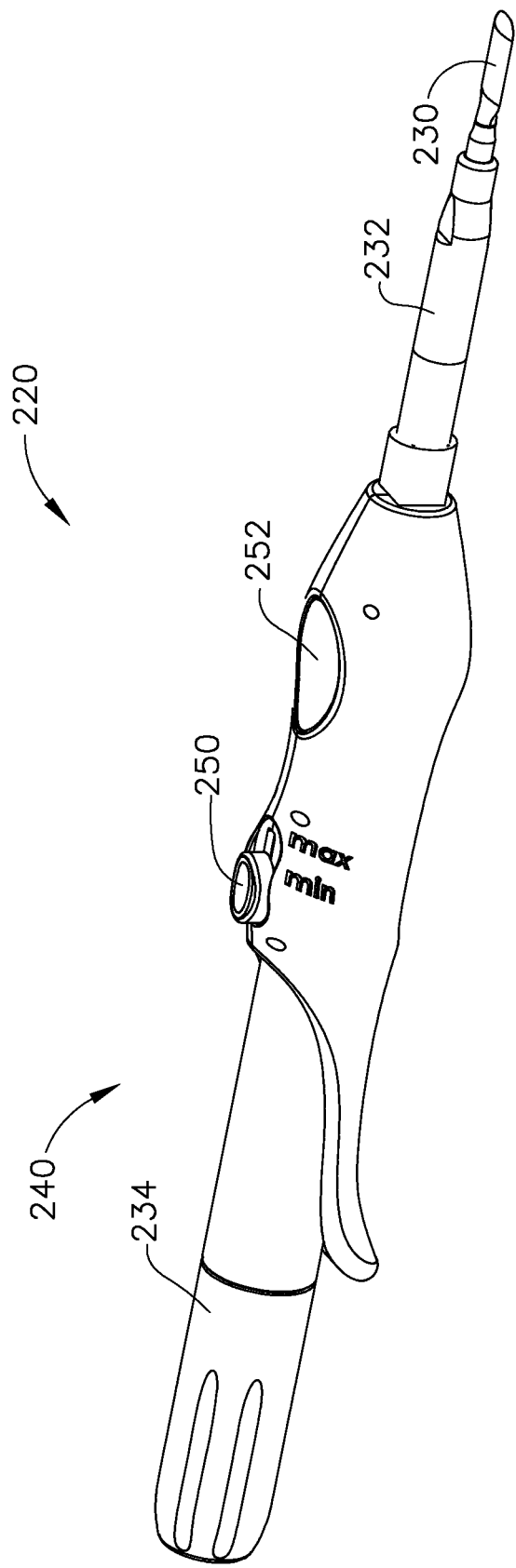
FIG. 5 depicts a perspective view of another exemplary ultrasonic surgical device, having a control slider and a recessed activation switch.

III. Exemplary Ultrasonic Surgical Instrument with Control Slider and Recessed Activation Button FIG. 5 depicts another exemplary ultrasonic surgical instrument (220), comprising a blade (230) positioned distally relative to a handpiece (240). An ultrasonic transducer (not shown) is positioned within handpiece (240), and may be coupled with an ultrasonic generator (not shown) in accordance with the teachings herein. An ultrasonic waveguide (not shown) is positioned within a sheath (232), which extends distally from handpiece (240). The ultrasonic waveguide couples the ultrasonic transducer with blade (230) in accordance with the teachings herein. It should therefore be understood that an ultrasonic generator may be used to activate the ultrasonic transducer in handpiece (240), and that the activated ultrasonic transducer may transmit ultrasonic vibration to blade (230) via the ultrasonic waveguide in accordance with the teachings herein. Handpiece (240) may be configured to substantially isolate the hand of the user relative to these ultrasonic vibrations. It should also be understood that ultrasonically vibrating blade (230) may be used to perform a variety of surgical procedures. Various other components that may be incorporated into handpiece (240), including but not limited to various components and configurations of electric circuitry, will be apparent to those of ordinary skill in the art in view of the teachings herein.

Instrument (220) of the present example also includes a rotation knob (234), which is operable to rotate blade (230) relative to handpiece (240) to provide a selected rotational orientation of rotate blade (230) relative to handpiece (240). For instance, instrument (220) may be configured such that knob (234) and blade (230) both rotate together unitarily or concomitantly. Rotation knob (234) and handpiece (240) may include complementary detent features or other features that permit rotation of knob (234) relative to handpiece (240) while also resisting inadvertent rotation of knob (234) relative to handpiece during surgical procedures. Of course, as with other components described herein, knob (234) is merely optional. For instance, in some versions where knob (234) is omitted, the ultrasonic transducer may protrude proximally from the proximal end of handpiece (240), similar to item (234) shown in FIG. 5.

Instrument (220) of the present example further comprises a control selector (250) and an activation button (252). Control selector (250) of this example comprises a slider that is operable to translate distally and proximally relative to handpiece (240) in order to select a desired level of ultrasonic energy to be applied to blade (230). In particular, control selector (250) may be toggled to a distal position to select a "maximum" level of ultrasonic energy; or to a proximal position to select a "minimum" level of ultrasonic energy. While control selector (250) provides selection of only two levels in this example, it should be understood that control selector (250) may provide selection of any other suitable number of levels. Furthermore, various ways in which manipulation of control selector (250) may affect electrical power provided to the ultrasonic transducer will be apparent to those of ordinary skill in the art in view of the teachings herein. By way of example only, instrument (220) may include circuitry similar to that described above and shown in FIG. 2. Other suitable circuitry that may be in communication with control selector (250) will be apparent to those of ordinary skill in the art in view of the teachings herein.

Activation button (252) is operable to selectively activate the ultrasonic transducer, to thereby selectively activate blade (230). For instance, activation button (252) may act as a switch selectively coupling the ultrasonic transducer with the ultrasonic generator. Activation button (252) may take a variety of forms. In some versions, activation button (252) comprises a capacitive switch. Thus, the use of the term "button" herein should not be read as requiring an electromechanical button, such as a movable component that is resiliently biased to separate one electrical contact from another electrical contact. Indeed, some versions of activation button (252) that comprise a capacitive switch may be activated without a user even making contact with activation button (252). That is, in some such versions, a user may simply bring their finger within sufficient proximity of activation button (252) in order to "actuate" activation button (252). In the present example, activation button (252) is recessed in handpiece (240). In versions such as those where activation button (252) comprises a capacitive switch, such a recessed positioning of activation button (252) may reduce the likelihood of (if not prevent) inadvertent actuation of activation button (252), such as might otherwise occur if instrument (220) is set on a tabletop surface with activation button (252) facing down. In some other versions, activation button (252) is not recessed in handpiece (240).

Regardless of whether activation button (252) is recessed, handpiece (240) may further comprise a slidable or otherwise movable cover that is operable to selectively cover activation button (252). In versions where activation button (252) comprises a capacitive switch, such a movable cover may be spaced sufficiently far away from activation button (252) that the presence of the movable cover over activation button (252) does not actuate activation button (252). In addition to or as an alternative to a capacitive switch, activation button (252) may further comprise a resistive sensor, such as a strain gauge or sensor that measures the resistance across a plane of pressure sensitive material. For instance, activation button (252) may be "actuated" when sufficient strain is placed on the strain gauge (or other type of resistive sensor) by a user's finger. A strain gauge (or other type of resistive sensor) may thus reduce the likelihood of (if not prevent) inadvertent actuation of activation button (252), such as might otherwise occur if instrument (220) is set on a tabletop surface with activation button (252) facing down. While a resistive sensor may be used for activation button (252) in lieu of a capacitive switch in some versions, some other versions of activation button (252) may include both a resistive sensor and a capacitive switch, such that the resistive sensor may provide confirmation that a finger (e.g., rather than an accidental fluid) is the source of the dielectric change sensed by the capacitive switch.

In addition or in the alternative, activation button (252) may comprise resonant cavity switching technology, infrared sensing technology, technology that uses a resonant, standing wave on a surface that is perturbed by the presence of a finger, and or any other suitable type of technology. Still other suitable types of switches, sensors, or other technology that may be incorporated into activation button (252) will be apparent to those of ordinary skill in the art in view of the teachings herein. Similarly, various ways in which such various types of activation button (252) components may be incorporated into the circuitry of instrument (220), as well as various circuit components that may accompany or be coupled with variations of activation button (252), will be apparent to those of ordinary skill in the art in view of the teachings herein.

In some versions, instrument (220) is configured such that a user must be continuously "actuating" activation button (252) in order for blade (230) to remain ultrasonically activated. In other words, instrument (220) may be configured such that blade (230) is only ultrasonically activated while the user is "actuating" activation button (252); and such that blade (230) is deactivated when the user removes his or her finger from activation button (252). In some other versions, instrument (220) is configured such that the user need only "actuate" activation button (252) a first time in order to ultrasonically activate blade (230). The user may then move his or her hand about handpiece (240) without having to engage activation button (252), with blade (230) remaining ultrasonically activated until the user re-engages activation button (252) again to deactivate blade (230). Circuitry in handpiece (240) may also comprise a logic configured to sense "taps" by the user on activation button (252), and activate blade (230) accordingly. For instance, such a logic may cause blade (230) to be ultrasonically activated when the user taps activation button (252) once; and cause blade (230) to be deactivated when the user taps activation button (252) twice (or vice-versa). Of course, such a control logic may alternatively require any other number of taps or tapping patterns to provide selective activation/deactivation of blade (230). Still other ways in which activation button (252) (and associated logic/circuitry) may provide selective activation/deactivation of blade (230) will be apparent to those of ordinary skill in the art in view of the teachings herein.

Handpiece (240) of the present example may be gripped by the user in a variety of ways. By way of example only, a user may grip handpiece like a pencil, with a single hand, with handpiece (240) resting in the crook of the user's hand between the user's thumb and index finger, and use their index finger or any other finger to "actuate" activation button (252). As another merely illustrative example, the user may grip handpiece (240) with their palm around handpiece (240), such that their thumb is used to "actuate" activation button (252). Alternatively, any other suitable gripping technique may be used.

Figure 6:
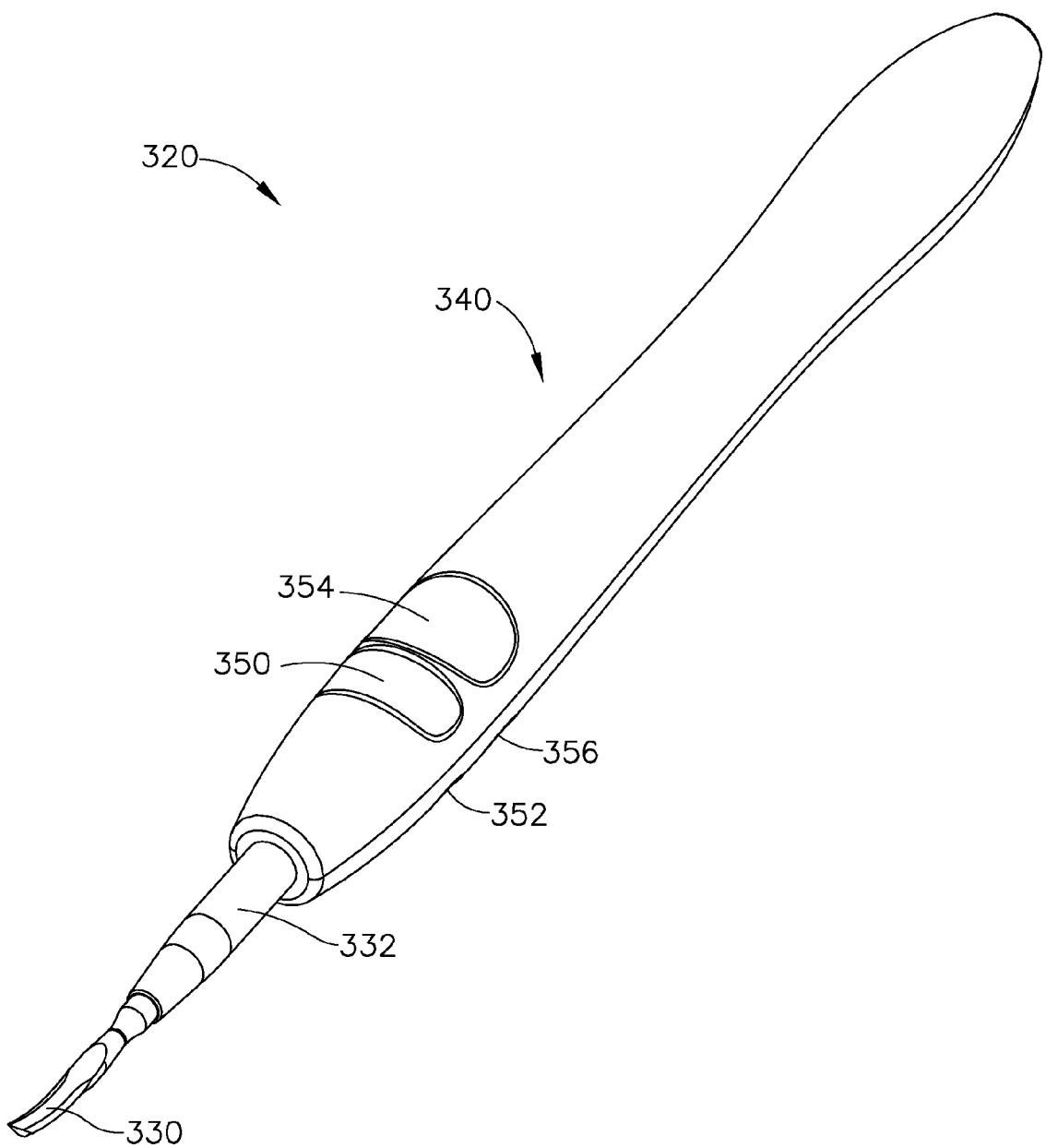
FIG. 6 depicts a perspective view of another exemplary ultrasonic surgical device, having a set of recessed switches.

IV. Exemplary Ultrasonic Surgical Instrument with Recessed Activation and Control Buttons FIG. 6 depicts another exemplary ultrasonic surgical instrument (320), comprising a blade (330) positioned distally relative to a handpiece (340). An ultrasonic transducer (not shown) is positioned within handpiece (340), and may be coupled with an ultrasonic generator (not shown) in accordance with the teachings herein. An ultrasonic waveguide (not shown) is positioned within a sheath (332), which extends distally from handpiece (340). The ultrasonic waveguide couples the ultrasonic transducer with blade (330) in accordance with the teachings herein. It should therefore be understood that an ultrasonic generator may be used to activate the ultrasonic transducer in handpiece (340), and that the activated ultrasonic transducer may transmit ultrasonic vibration to blade (330) via the ultrasonic waveguide in accordance with the teachings herein. Handpiece (340) may be configured to substantially isolate the hand of the user relative to these ultrasonic vibrations. It should also be understood that ultrasonically vibrating blade (330) may be used to perform a variety of surgical procedures. Various other components that may be incorporated into handpiece (340), including but not limited to various components and configurations of electric circuitry, will be apparent to those of ordinary skill in the art in view of the teachings herein.

Instrument (320) of the present example further comprises a control and activation buttons (350, 352, 354, 356). Control and activation buttons (350, 352, 354, 356) are provided in opposing pairs in this example. In particular, control and activation buttons (350, 352) are positioned at a first common longitudinal position but are on opposing sides of handpiece (340); while control and activation buttons (354, 356) are positioned at a second common longitudinal position but are on opposing sides of handpiece (340). In the present example, control and activation buttons (350, 352, 354, 356) are operable to simultaneously ultrasonically activate blade (330) and select a desired level of ultrasonic energy to be applied to blade (230). For instance, either or both control and activation buttons (350, 352) may be "actuated" to simultaneously select a "minimum" level of ultrasonic energy and ultrasonically activate blade (230) with the selected "minimum" level of ultrasonic energy; while either or both activation buttons activation buttons (354, 356) may be "actuated" to simultaneously select a "maximum" level of ultrasonic energy and ultrasonically activate blade (230) with the selected "maximum" level of ultrasonic energy. Alternatively, these roles may be reversed, such that buttons (350, 352) are associated with a "maximum" level of ultrasonic energy while buttons (354, 356) are associated with a "minimum" level of ultrasonic energy. It should also be understood that additional activation and control buttons may be included to provide more than two ultrasonic energy levels/amplitudes to choose from.

As with other activation buttons/features described herein, control and activation buttons (350, 352, 354, 356) may act as switches selectively coupling the ultrasonic transducer with the ultrasonic generator. Similarly, control and activation buttons (350, 352, 354, 356) may take a variety of forms. By way of example only, control and activation buttons (350, 352, 354, 356) may comprise capacitive switches; resistive sensors; resonant cavity switching technology; infrared sensing technology; technology that uses a resonant, standing wave on a surface that is perturbed by the presence of a finger; and/or any other suitable type of technology. Still other suitable types of switches, sensors, or other technology that may be incorporated into control and activation buttons (350, 352, 354, 356) will be apparent to those of ordinary skill in the art in view of the teachings herein. Similarly, various ways in which such various types of control and activation button (350, 352, 354, 356) components may be incorporated into the circuitry of instrument (320), as well as various circuit components that may accompany or be coupled with variations of control and activation buttons (350, 352, 354, 356), will be apparent to those of ordinary skill in the art in view of the teachings herein.

As is also shown in FIG. 6, control and activation buttons (350, 352, 354, 356) are recessed in handpiece (340). As described elsewhere herein, such a recessed positioning of control and activation buttons (350, 352, 354, 356) may reduce the likelihood of (if not prevent) inadvertent actuation of control and activation buttons (350, 352, 354, 356), such as might otherwise occur if instrument (320) is set on a tabletop surface with control and activation buttons (350, 352, 354, 356) facing down. In some other versions, control and activation buttons (350, 352, 354, 356) are not recessed in handpiece (340). As also described elsewhere herein, handpiece (340) may further comprise a slidable or otherwise movable cover that is operable to selectively cover control and activation buttons (350, 352, 354, 356).

In some versions, instrument (220) is configured such that the user must "actuate" either both opposing control and activation buttons (350, 352) together simultaneously, or both opposing control and activation buttons (354, 356) together simultaneously, in order to ultrasonically activate blade (330). Requiring simultaneous "actuation" of control and activation buttons (350, 352, 354, 356) in opposing pairs may thus also reduce the likelihood of (if not prevent) inadvertent "actuation" of control and activation buttons (350, 352, 354, 356). Alternatively, instrument (220) may be configured such that only one selected control and activation button (350, 352, 354, 356) need be "actuated" in order to ultrasonically activate blade (330). In either case, the opposing positioning of control and activation buttons (350, 352, 354, 356) may allow the user to rotate the entire handpiece (340) in the user's hand (e.g., about the axis defined by handpiece (340)), such as to re-orient blade (330) to a selected rotational orientation, while still allowing control and activation buttons (350, 352, 354, 356) to be reached and manipulated with relative ease with handpiece (340) in different rotational orientations.

As described above with respect to instrument (220), instrument (320) may be configured such that a user must be continuously "actuating" one or two control and activation buttons (350, 352, 354, 356) in order for blade (330) to remain ultrasonically activated. Alternatively, instrument (320) may be configured such that the user need only "actuate" one or two control and activation buttons (350, 352, 354, 356) a first time in order to ultrasonically activate blade (330). The user may then move his or her hand about handpiece (340) without having to engage one or two control and activation buttons (350, 352, 354, 356), with blade (330) remaining ultrasonically activated until the user re-engages one or two control and activation buttons (350, 352, 354, 356) again to deactivate blade (330). As yet another merely illustrative alternative, circuitry in handpiece (340) may comprise a logic configured to sense "taps" by the user on one or two control and activation buttons (350, 352, 354, 356), and activate blade (330) accordingly as described elsewhere herein. Still other ways in which control and activation buttons (350, 352, 354, 356) (and associated logic/circuitry) may provide selective activation/deactivation of blade (330) will be apparent to those of ordinary skill in the art in view of the teachings herein. Similarly, various components and configurations of circuitry that may be in communication with control and activation buttons (350, 352, 354, 356) will be apparent to those of ordinary skill in the art in view of the teachings herein.

Handpiece (340) of the present example may be gripped by the user in a variety of ways. By way of example only, a user may grip handpiece like a pencil, with a single hand, with handpiece (340) resting in the crook of the user's hand between the user's thumb and index finger, such that the user's thumb and/or the tip of another finger is used to "actuate" one or two control and activation buttons (350, 352, 354, 356). As another merely illustrative example, the user may grip handpiece (340) with their palm around handpiece (340), such that the user's thumb and/or the side of another finger is used to "actuate" one or two control and activation buttons (350, 352, 354, 356). Alternatively, any other suitable gripping technique may be used.

Figure 7:
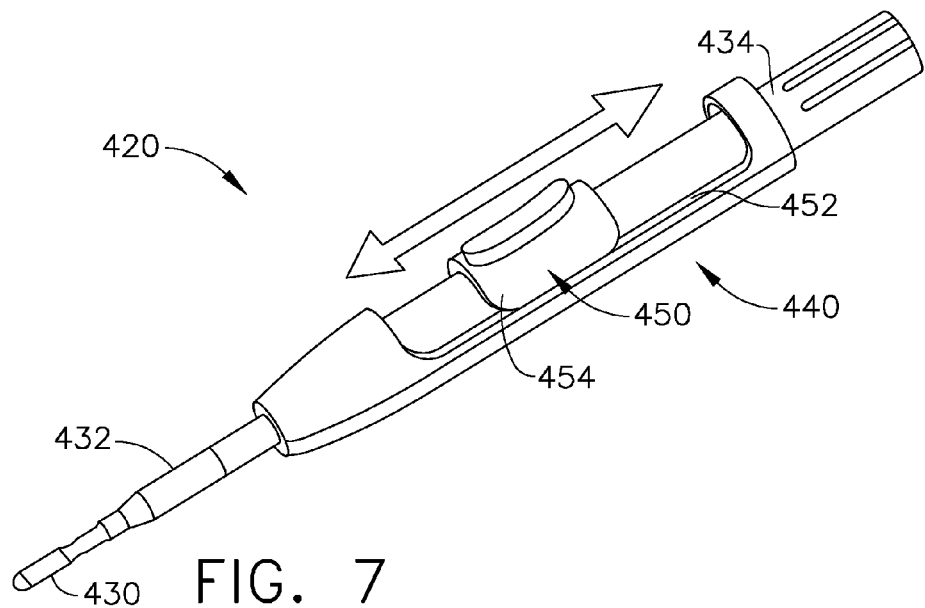
FIG. 7 depicts a perspective view of another exemplary ultrasonic surgical device, having a slidable activation button.
Figure 8:
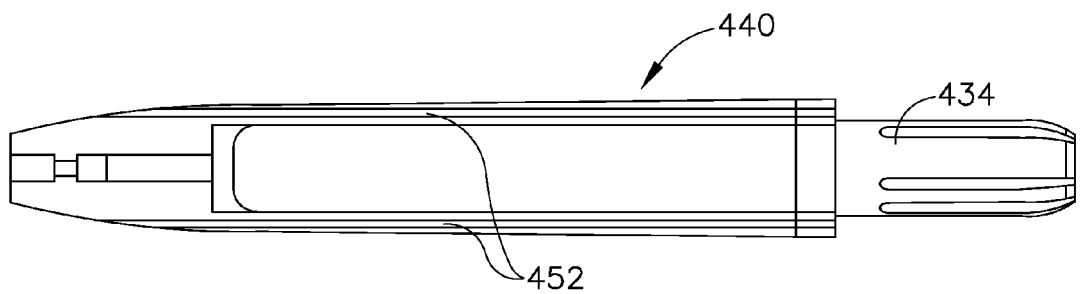
FIG. 8 depicts a cutaway elevation view of the ultrasonic surgical device of FIG. 7, showing exemplary magnetic rail connections.
Figure 9:
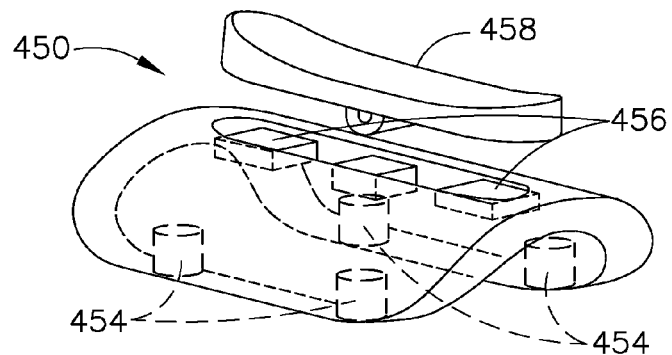
FIG. 9 depicts an enlarged perspective view of the activation button assembly of the ultrasonic surgical device of FIG. 7.

V. Exemplary Ultrasonic Surgical Instrument with Sliding Activation and Control Button FIGS. 7-9 depict another exemplary ultrasonic surgical instrument (420), comprising a blade (430) positioned distally relative to a handpiece (440). An ultrasonic transducer (not shown) is positioned within handpiece (440), and may be coupled with an ultrasonic generator (not shown) in accordance with the teachings herein. An ultrasonic waveguide (not shown) is positioned within a sheath (432), which extends distally from handpiece (440). The ultrasonic waveguide couples the ultrasonic transducer with blade (430) in accordance with the teachings herein. It should therefore be understood that an ultrasonic generator may be used to activate the ultrasonic transducer in handpiece (440), and that the activated ultrasonic transducer may transmit ultrasonic vibration to blade (430) via the ultrasonic waveguide in accordance with the teachings herein. Handpiece (440) may be configured to substantially isolate the hand of the user relative to these ultrasonic vibrations. It should also be understood that ultrasonically vibrating blade (430) may be used to perform a variety of surgical procedures. Various other components that may be incorporated into handpiece (440), including but not limited to various components and configurations of electric circuitry, will be apparent to those of ordinary skill in the art in view of the teachings herein.

Instrument (420) of the present example also includes a rotation knob (434), which is operable to rotate blade (430) relative to handpiece (440) to provide a selected rotational orientation of rotate blade (430) relative to handpiece (440). For instance, instrument (420) may be configured such that knob (434) and blade (430) both rotate together unitarily or concomitantly. Rotation knob (434) and handpiece (440) may include complementary detent features or other features that permit rotation of knob (434) relative to handpiece (440) while also resisting inadvertent rotation of knob (434) relative to handpiece during surgical procedures. Of course, as with other components described herein, knob (434) is merely optional. For instance, in some versions where knob (434) is omitted, the ultrasonic transducer may protrude proximally from the proximal end of handpiece (440), similar to item (434) shown in FIGS. 7-8.

Instrument (420) of the present example further comprises a removable activation button assembly (450), which translates longitudinally along metal rails (452) carried by handpiece (440). Rails (452) are electrically connected to the ultrasonic transducer (not shown) as would be readily apparent to one of ordinary skill in the art in view of the teachings herein. Activation button assembly (450) contains one or more magnets (454) to anchor onto and form an electrical connection with metal rails (452). Magnet (454) is covered in an electrically conductive material and wired to dome switches (456). Dome switches (456) selectively are activated by, a rocker switch (458) in this example, though it should be understood that any other suitable type of switch may be used. Activation button assembly (450) may be longitudinally moved in a sliding fashion relative to handpiece (440) to any place on instrument (420) where magnet (454) holds button assembly (450) in place on metal rails (452). This allows for a variable distance between blade (430) and button assembly (450). Activation button assembly (450) may be configured such that blade (430) is ultrasonically activated when rocker switch (458) is actuated to actuate a selected dome switch (458). The direction in which rocker switch (458) is rocked determines which dome switch (458) will be actuated, which will in turn determine whether blade (430) is activated at a "maximum" or "minimum" level of ultrasonic energy.

Alternatively, rocker switch (458) and dome switches (458) may be replaced with a single switch. For instance, such a single switch may include a conventional electromechanical button or any other type of "button," including but not limited to a capacitive switch; a resistive sensor; resonant cavity switching technology; infrared sensing technology; technology that uses a resonant, standing wave on a surface that is perturbed by the presence of a finger; and/or any other suitable type of technology. Still other suitable types of switches, sensors, or other technology that may be incorporated into rocker switch (458) will be apparent to those of ordinary skill in the art in view of the teachings herein. Such a single switch may be configured and operable in accordance with activation button (252), described above, or in any other suitable fashion. In some such versions, the energy level at which blade (430) will be activated may be based at least in part of the longitudinal position of button assembly (450) on rails (452). For instance, when button assembly (450) is located in a distal position, actuation of button assembly (450) may result in ultrasonic activation of blade (430) at a "maximum" level of ultrasonic energy. When button assembly (450) is located in a proximal position, actuation of button assembly (450) may result in ultrasonic activation of blade (430) at a "minimum" level of ultrasonic energy. Of course, the distal/proximal and maximum/minimum relationship may be reversed. Furthermore, instrument (420) may be configured such that the level of ultrasonic energy may be varied between the "maximum" level and the "minimum" level by longitudinally positioning button assembly (450) at a selected longitudinal position between a distal-most and proximal-most position. For instance, one or more position sensors or other types of components may be configured to sense the longitudinal position of button assembly (450) along rails (452), and circuitry of instrument (420) may effect adjustment of the level of ultrasonic energy accordingly.

In some versions of instrument (420) where the level of ultrasonic energy applied to blade (430) is based at least in part of the longitudinal position of button assembly (450) along rails (452), the available energy levels may be discrete and predetermined. For instance, a first discrete and predetermined level of ultrasonic energy may be associated with button assembly (450) being positioned within a first longitudinal range, with a second discrete and predetermined level of ultrasonic energy being associated with button assembly (450) being positioned within a second longitudinal range, and a third discrete and predetermined level of ultrasonic energy being associated with button assembly (450) being positioned within a third longitudinal range, etc. Alternatively, the available ultrasonic energy levels may be virtually infinitely variable within a predetermined range. For instance, the ultrasonic energy level may be a substantially linear function of the longitudinal position of button assembly (450) along rails (452), such that the ultrasonic energy level progressively and substantially continuously increases or decreases as button assembly (450) is slid along rails (452). Still other suitable ways in which the ultrasonic energy level of blade (430) may be based at least in part on the longitudinal position of button assembly (450) along rails (452) will be apparent to those of ordinary skill in the art in view of the teachings herein. Similarly, various suitable components and configurations of circuitry that may be in communication with button assembly (450) will be apparent to those of ordinary skill in the art in view of the teachings herein. By way of example only, a variable resistor, variable capacitor, variable inductor, and/or some other type(s) of circuit component(s) may be responsive to the longitudinal position of button assembly (450) along rails (452), and may provide a virtually infinitely variable level of electrical power (within a predefined range) to the ultrasonic transducer in the handpiece (440), which may thereby provide a virtually infinitely variable level of ultrasonic energy (within a predefined range) at blade (430).

Handpiece (440) of the present example may be gripped by the user in a variety of ways. By way of example only, a user may grip handpiece like a pencil, with a single hand, with handpiece (440) resting in the crook of the user's hand between the user's thumb and index finger, such that the user's thumb and/or the tip of another finger is used to "actuate" button assembly (450). As another merely illustrative example, the user may grip handpiece (440) with their palm around handpiece (440), such that the user's thumb and/or the side of another finger is used to "actuate" button assembly (450). Alternatively, any other suitable gripping technique may be used.

Figure 10:
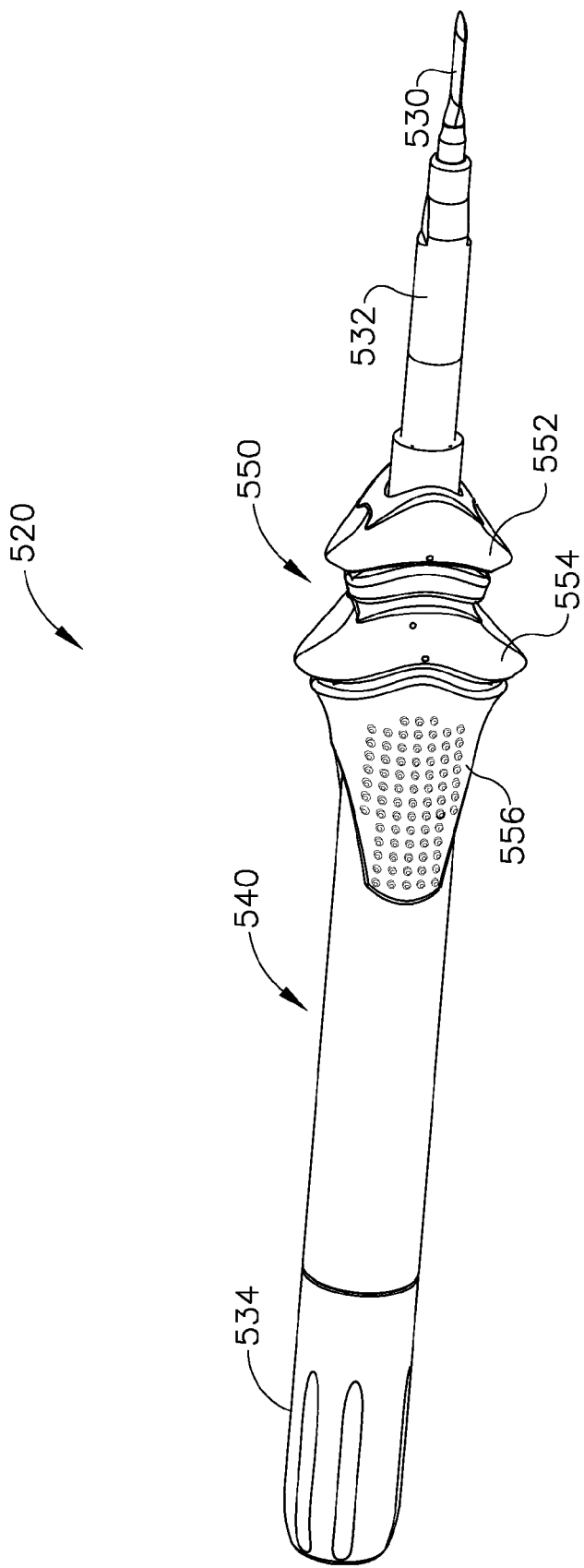
FIG. 10 depicts a perspective view of another exemplary ultrasonic surgical device, having a control and activation slider.

VI. Exemplary Ultrasonic Surgical Instrument with Flared Push-Pull Slide Control and Activation FIG. 10 depicts another exemplary ultrasonic surgical instrument (520), comprising a blade (530) positioned distally relative to a handpiece (540). An ultrasonic transducer (534) is secured to handpiece (540), and may be coupled with an ultrasonic generator (not shown) in accordance with the teachings herein. An ultrasonic waveguide (not shown) is positioned within a sheath (532), which extends distally from handpiece (540). The ultrasonic waveguide couples ultrasonic transducer (534) with blade (530) in accordance with the teachings herein. It should therefore be understood that an ultrasonic generator may be used to activate ultrasonic transducer (534) of handpiece (540), and that the activated ultrasonic transducer (534) may transmit ultrasonic vibration to blade (530) via the ultrasonic waveguide in accordance with the teachings herein. Handpiece (540) may be configured to substantially isolate the hand of the user relative to these ultrasonic vibrations. It should also be understood that ultrasonically vibrating blade (530) may be used to perform a variety of surgical procedures. Various other components that may be incorporated into handpiece (540), including but not limited to various components and configurations of electric circuitry, will be apparent to those of ordinary skill in the art in view of the teachings herein.

Instrument (520) of the present example further comprises a control and activation slider (550). Control and activation slider (550) comprises a distal flared portion (552), a proximal flared portion (554), and a knurled gripping portion (556). Control and activation slider (550) may include rubber or a similar material on its exterior to facilitate gripping. In some versions, control and activation slider (550) is formed as a unitary component, such that distal flared portion (552), proximal flared portion (554), and gripping portion (556) all translate together unitarily relative to handpiece (540). In some other versions, control and activation slider (550) is formed as separate parts that are movable relative to each other (in addition to being movable relative to handpiece (540)). For instance, distal flared portion (552) may be translatable relative to handpiece (540), independently of proximal flared portion (554); while proximal flared portion (554) may be translatable relative to handpiece (540) independently of distal flared portion (552). In either case, control and activation slider (550) may be operable to act as a switch selectively coupling ultrasonic transducer (534) with the ultrasonic generator. In particular, control and activation slider (550)

may be operable to simultaneously ultrasonically activate blade (530) and select a desired level of ultrasonic energy to be applied to blade (530).

In some versions, control and activation slider (550) is movable among three selectable longitudinal positions relative to handpiece (540). For instance, instrument (520) may be configured such that moving control and activation slider (550) to a distal position activates blade (530) to ultrasonically vibrate at a "maximum" level of ultrasonic energy; such that moving control and activation slider (550) to a proximal position activates blade (530) to ultrasonically vibrate at a "minimum" level of ultrasonic energy; and such that blade (530) is deactivated when control and activation slider (550) is at a middle position between the distal and proximal positions. Of course, more than three selectable longitudinal positions may be provided, along with more than three corresponding selectable levels of ultrasonic energy. Furthermore, any suitable relationship between the longitudinal position of control and activation slider (550) and the ultrasonic energy level at which blade (530) is activated may be used. By way of example only, instrument (520) may be configured such that distal positioning of control and activation slider (550) provides a "maximum" level of ultrasonic energy at blade (530), middle positioning of control and activation slider (550) provides a "minimum" level of ultrasonic energy at blade (530), and proximal positioning of control and activation slider (550) causes blade (530) to be ultrasonically inactive.

To the extent that the available levels of ultrasonic energy are discrete and predetermined, control and activation slider (550) and handpiece (540) may include complementary detent features or other features to provide tactile feedback to the user and/or to provide at least some degree of resistance to longitudinal movement of control and activation slider (550) relative to handpiece (540) (e.g., to reduce the likelihood of inadvertent sliding of control and activation slider (550), etc.). Alternatively, the available ultrasonic energy levels may be virtually infinitely variable within a predetermined range, with the energy level being based at least in part on the longitudinal position of control and activation slider (550) relative to handpiece (540). For instance, blade (530) may be deactivated when control and activation slider (550) is at a proximal-most position, and the level ultrasonic energy applied to blade (530) may progressively and substantially continuously increase as control and activation slider (550) is moved distally, until control and activation slider (550) reaches a distal-most position where the level of ultrasonic energy is at its maximum. Still other suitable ways in which the ultrasonic energy level of blade (530) may be based at least in part on the longitudinal position of control and activation slider (550) relative to handpiece (540) will be apparent to those of ordinary skill in the art in view of the teachings herein.

In some other versions, distal flared portion (552) is movable independently relative to proximal flared portion (554). In some such versions, one portion (552 or 554) may be used as an ultrasonic energy level selector and the other portion (552 or 554) may be used to selectively activate blade (530). For instance, instrument (520) may be configured such that proximal flared portion (554) may be slid relative to handpiece (540) to select a level of ultrasonic energy to be applied to blade (530); while distal flared portion (552) may be slid relative to handpiece (540) to selectively activate (530) blade (e.g., turn blade (530) "on or off"). Of course, these roles could be reversed. In still other versions, one portion (552 or 554) may be movable relative to handpiece (540) to activate blade (530) at a selected level of ultrasonic energy while the other portion (552 or 554) remains longitudinally fixed to handpiece (540), such as to serve as a grip during use of instrument (520). Still other suitable ways in which control and activation slider (550) may be configured and operable will be apparent to those of ordinary skill in the art in view of the teachings herein. Similarly, various suitable components and configurations of circuitry that may be in communication with control and activation slider (550) will be apparent to those of ordinary skill in the art in view of the teachings herein. By way of example only, a variable resistor and/or some other type(s) of circuit component(s) may be responsive to the longitudinal position of control and activation slider (550) (or portions thereof), and may provide a virtually infinitely variable level of electrical power (within a predefined range) to the ultrasonic transducer in the handpiece (540), which may thereby provide a virtually infinitely variable level of ultrasonic energy (within a predefined range) at blade (530).

Handpiece (540) of the present example may be gripped by the user in a variety of ways. By way of example only, a user may grip handpiece (540) like a pencil, with a single hand, with handpiece (540) resting in the crook of the user's hand between the user's thumb and index finger, such that the user's thumb and/or the tip of another finger is used to "actuate" control and activation slider (550). As another merely illustrative example, the user may grip handpiece (540) with their palm around handpiece (540), such that the user's thumb and/or the side of another finger is used to "actuate" control and activation slider (550). In either case, the user may grip gripping portion (556) (or any other portion of handpiece (540)) during use of instrument (520). It should also be understood that the configuration of control and activation slider (550) may permit the user to rotate the entire handpiece (540) in the user's hand (e.g., about the longitudinal axis defined by handpiece (540)), such as to re-orient blade (530) to a selected rotational orientation, while still allowing control and activation slider (550) to be reached and manipulated with relative ease with handpiece (540) in different rotational orientations. Of course, any suitable gripping technique may be used.

Figure 11:
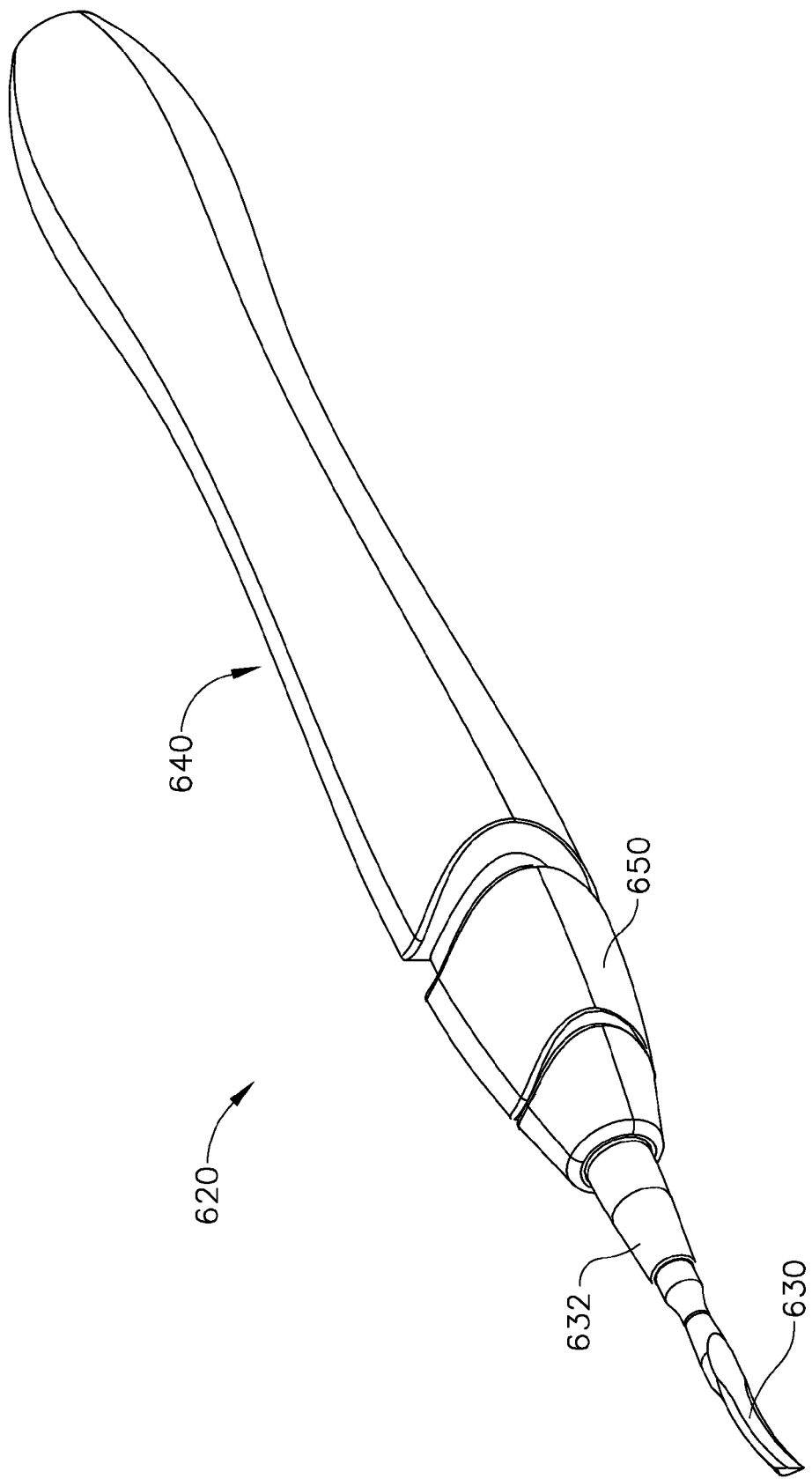
FIG. 11 depicts a perspective view of another exemplary ultrasonic surgical device, having a control and activation slider.
Figure 12:
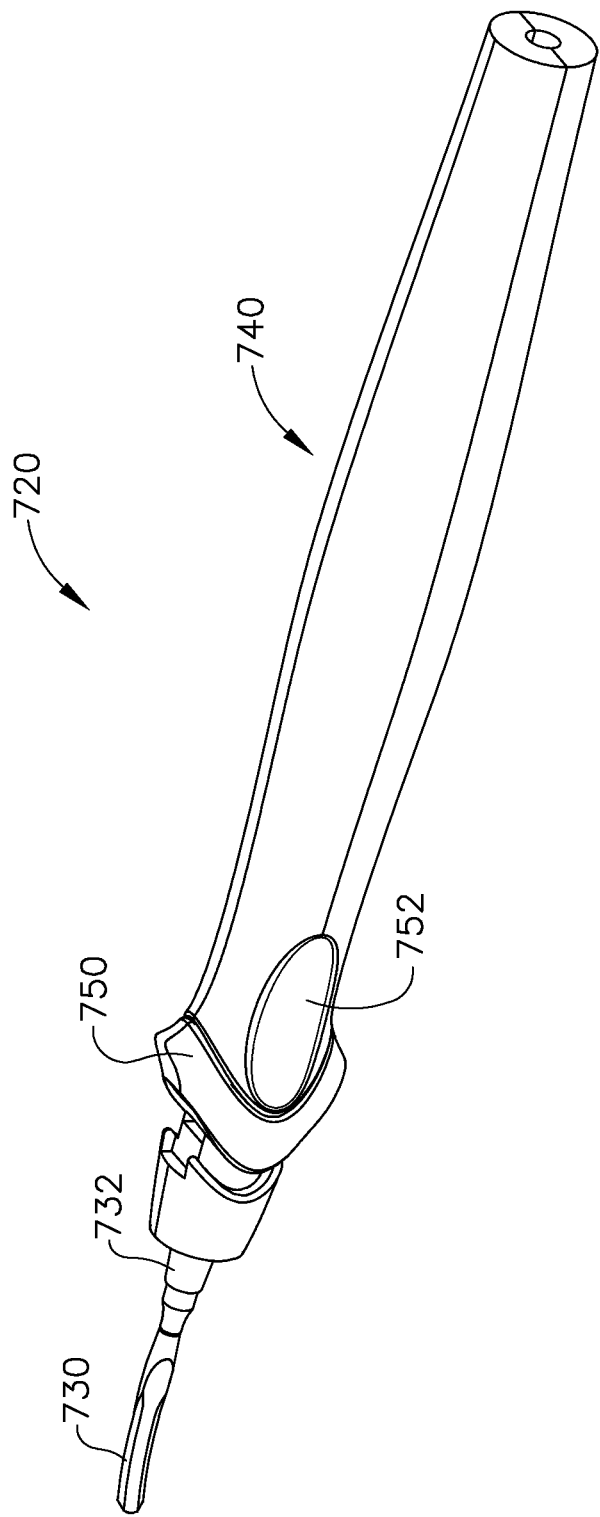
FIG. 12 depicts a perspective view of another exemplary ultrasonic surgical device, having a control slider and an activation button.

VII. Exemplary Ultrasonic Surgical Instrument with Flush Push-Pull Slide Control and Activation FIG. 11 depicts another exemplary ultrasonic surgical instrument (620), comprising a blade (630) positioned distally relative to a handpiece (640). An ultrasonic transducer (not shown) is secured in handpiece (640), and may be coupled with an ultrasonic generator (not shown) in accordance with the teachings herein. An ultrasonic waveguide (not shown) is positioned within a sheath (632), which extends distally from handpiece (640). The ultrasonic waveguide couples the ultrasonic transducer with blade (630) in accordance with the teachings herein. It should therefore be understood that an ultrasonic generator may be used to activate the ultrasonic transducer of handpiece (640), and that the activated ultrasonic transducer may transmit ultrasonic vibration to blade (630) via the ultrasonic waveguide in accordance with the teachings herein. Handpiece (640) may be configured to substantially isolate the hand of the user relative to these ultrasonic vibrations. It should also be understood that ultrasonically vibrating blade (630) may be used to perform a variety of surgical procedures. Various other components that may be incorporated into handpiece (640), including but not limited to various components and configurations of electric circuitry, will be apparent to those of ordinary skill in the art in view of the teachings herein.

Instrument (620) of the present example further comprises a control and activation slider (650), which is substantially flush with the body of handpiece (640). Control and activation slider (650) is operable to act as a switch selectively coupling the ultrasonic transducer with the ultrasonic generator. In particular, control and activation slider (650) is operable to simultaneously ultrasonically activate blade (630) and select a desired level of ultrasonic energy to be applied to blade (630). In some versions, control and activation slider (550) is movable among three selectable longitudinal positions relative to handpiece (540). For instance, instrument (620) may be configured such that distal longitudinal positioning of control and activation slider (650) provides a "maximum" level of ultrasonic energy at blade (630), middle longitudinal positioning of control and activation slider (650) provides a "minimum" level of ultrasonic energy at blade (630), and proximal longitudinal positioning of control and activation slider (650) causes blade (630) to be ultrasonically inactive. Of course, more than three selectable longitudinal positions may be provided, along with more than three corresponding selectable levels of ultrasonic energy. Furthermore, any suitable relationship between the longitudinal position of control and activation slider (650) and the ultrasonic energy level at which blade (630) is activated may be used.

To the extent that the available levels of ultrasonic energy are discrete and predetermined, control and activation slider (650) and handpiece (640) may include complementary detent features or other features to provide tactile feedback to the user and/or to provide at least some degree of resistance to longitudinal movement of control and activation slider (650) relative to handpiece (640) (e.g., to reduce the likelihood of inadvertent sliding of control and activation slider (650), etc.). Alternatively, the available ultrasonic energy levels may be virtually infinitely variable within a predetermined range, with the energy level being based at least in part on the longitudinal position of control and activation slider (650) relative to handpiece (640). For instance, blade (630) may be deactivated when control and activation slider (650) is at a proximal-most position, and the level ultrasonic energy applied to blade (630) may progressively and substantially continuously increase as control and activation slider (650) is moved distally, until control and activation slider (650) reaches a distal-most position where the level of ultrasonic energy is at its maximum.

Still other suitable ways in which the ultrasonic energy level of blade (630) may be based at least in part on the longitudinal position of control and activation slider (650) relative to handpiece (640) will be apparent to those of ordinary skill in the art in view of the teachings herein. Furthermore, other suitable ways in which control and activation slider (650) may be configured and operable will be apparent to those of ordinary skill in the art in view of the teachings herein. Similarly, various suitable components and configurations of circuitry that may be in communication with control and activation slider (650) will be apparent to those of ordinary skill in the art in view of the teachings herein. By way of example only, a variable resistor and/or some other type(s) of circuit component(s) may be responsive to the longitudinal position of control and activation slider (650), and may provide a virtually infinitely variable level of electrical power (within a predefined range) to the ultrasonic transducer in the handpiece (640), which may thereby provide a virtually infinitely variable level of ultrasonic energy (within a predefined range) at blade (630).

Handpiece (640) of the present example may be gripped by the user in a variety of ways. By way of example only, a user may grip handpiece (640) like a pencil, with a single hand, with handpiece (640) resting in the crook of the user's hand between the user's thumb and index finger, such that the user's thumb and/or the tip of another finger is used to "actuate" control and activation slider (650). As another merely illustrative example, the user may grip handpiece (640) with their palm around handpiece (640), such that the user's thumb and/or the side of another finger is used to "actuate" control and activation slider (650). It should also be understood that the configuration of control and activation slider (650) may permit the user to rotate the entire handpiece (640) in the user's hand (e.g., about the longitudinal axis defined by handpiece (640)), such as to re-orient blade (630) to a selected rotational orientation, while still allowing control and activation slider (650) to be reached and manipulated with relative ease with handpiece (640) in different rotational orientations. Of course, any suitable gripping technique may be used.

VIII. Exemplary Ultrasonic Surgical Instrument with Flared Push-Pull Slide Control and Button Activation FIG. 11 depicts another exemplary ultrasonic surgical instrument (720), comprising a blade (730) positioned distally relative to a handpiece (740). An ultrasonic transducer (not shown) is secured in handpiece (740), and may be coupled with an ultrasonic generator (not shown) in accordance with the teachings herein. An ultrasonic waveguide (not shown) is positioned within a sheath (732), which extends distally from handpiece (740). The ultrasonic waveguide couples the ultrasonic transducer with blade (730) in accordance with the teachings herein. It should therefore be understood that an ultrasonic generator may be used to activate the ultrasonic transducer of handpiece (740), and that the activated ultrasonic transducer may transmit ultrasonic vibration to blade (730) via the ultrasonic waveguide in accordance with the teachings herein. Handpiece (740) may be configured to substantially isolate the hand of the user relative to these ultrasonic vibrations. It should also be understood that ultrasonically vibrating blade (730) may be used to perform a variety of surgical procedures. Various other components that may be incorporated into handpiece (740), including but not limited to various components and configurations of electric circuitry, will be apparent to those of ordinary skill in the art in view of the teachings herein.

Instrument (720) of the present example further comprises a control slider (750) and an activation button (750). Control slider (750) is operable to translate distally and proximally relative to handpiece (740) in order to select a desired level of ultrasonic energy to be applied to blade (730). In particular, control slider (750) may be toggled to a distal position to select a "maximum" level of ultrasonic energy; or to a proximal position to select a "minimum" level of ultrasonic energy. While control slider (750) provides selection of only two levels in this example, it should be understood that control slider (750) may provide selection of any other suitable number of levels. Furthermore, various ways in which manipulation of control slider (750) may affect electrical power provided to the ultrasonic transducer will be apparent to those of ordinary skill in the art in view of the teachings herein. By way of example only, instrument (720) may include circuitry similar to that described above and shown in FIG. 2. Other suitable circuitry that may be in communication with control slider (750) will be apparent to those of ordinary skill in the art in view of the teachings herein.

Activation button (752) is operable to selectively activate the ultrasonic transducer, to thereby selectively activate blade (730) at the level selected using control slider (750). For instance, activation button (752) may act as a switch selectively coupling the ultrasonic transducer with the ultrasonic generator. Activation button (752) may take a variety of forms. By way of example only, activation button (752) may comprise a conventional electromechanical button, a capacitive switch; a resistive sensor; resonant cavity switching technology; infrared sensing technology; technology that uses a resonant, standing wave on a surface that is perturbed by the presence of a finger; and/or any other suitable type of technology. Still other suitable types of switches, sensors, or other technology that may be incorporated into activation button (752) will be apparent to those of ordinary skill in the art in view of the teachings herein. Activation button (752) may be recessed within handpiece (740), if desired. In addition, a second activation button (752) may be provided on the opposite side of handpiece (740), if desired. For instance, such a pair of activation buttons (752) may be independently operable. Alternatively, instrument (740) may require both such buttons (752) to be "actuated" simultaneously in order for blade (730) to be activated. Various ways in which such various types of activation button (752) components may be incorporated into the circuitry of instrument (720), as well as various circuit components that may accompany or be coupled with variations of activation button (752), will be apparent to those of ordinary skill in the art in view of the teachings herein.

Handpiece (740) of the present example may be gripped by the user in a variety of ways. By way of example only, a user may grip handpiece (740) like a pencil, with a single hand, with handpiece (740) resting in the crook of the user's hand between the user's thumb and index finger. As another merely illustrative example, the user may grip handpiece (740) with their palm around handpiece (740). It should also be understood that the configuration of control and activation slider (750) may permit the user to rotate the entire handpiece (740) in the user's hand (e.g., about the longitudinal axis defined by handpiece (740)), such as to re-orient blade (730) to a selected rotational orientation, while still allowing control slider (750) and/or activation button (752) to be reached and manipulated with relative ease with handpiece (740) in different rotational orientations. Of course, any suitable gripping technique may be used.

Figure 13:
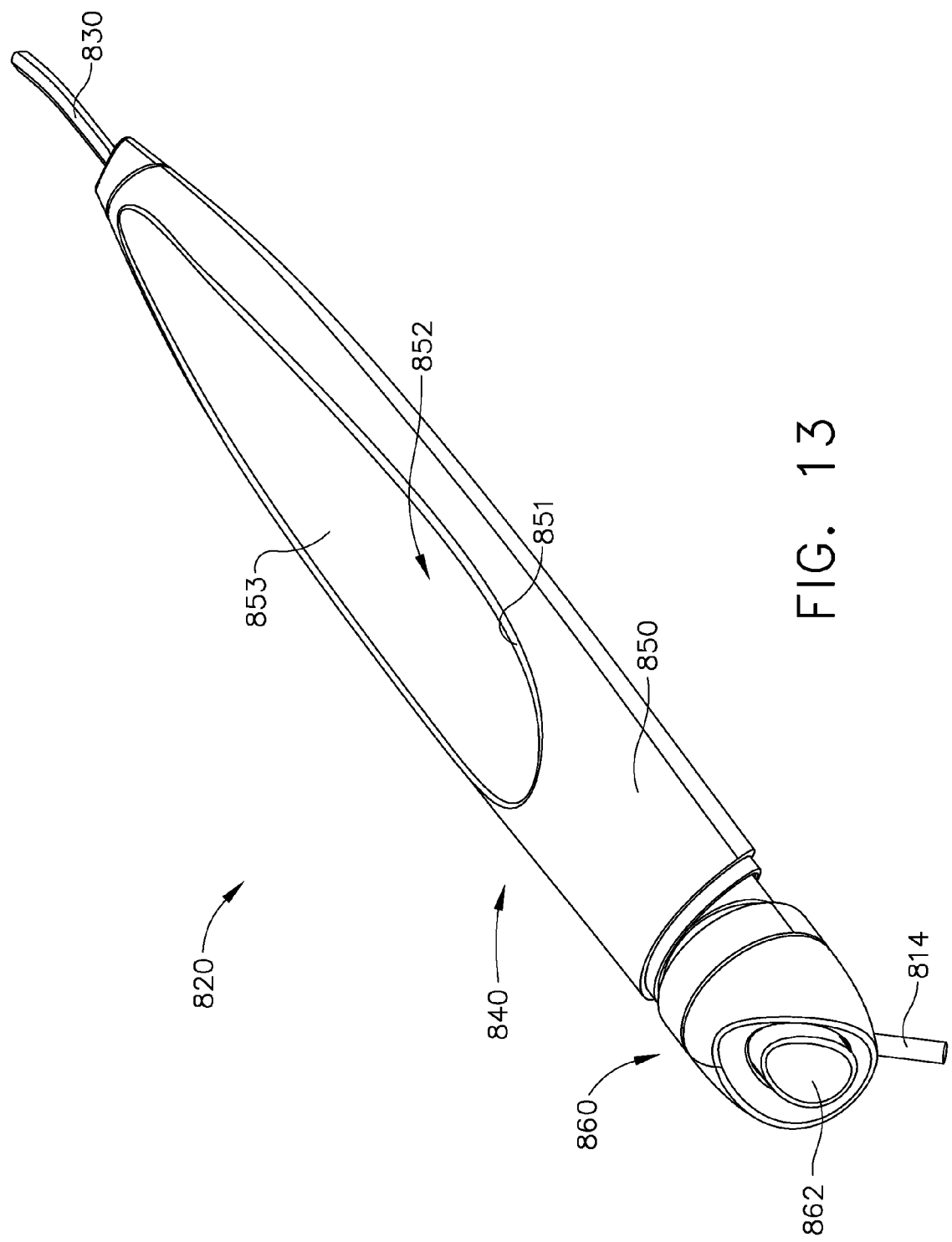
FIG. 13 depicts a perspective view of another exemplary ultrasonic surgical device, having a rotatable sheath and an elongate control and activation surface.
Figures 14, 15:
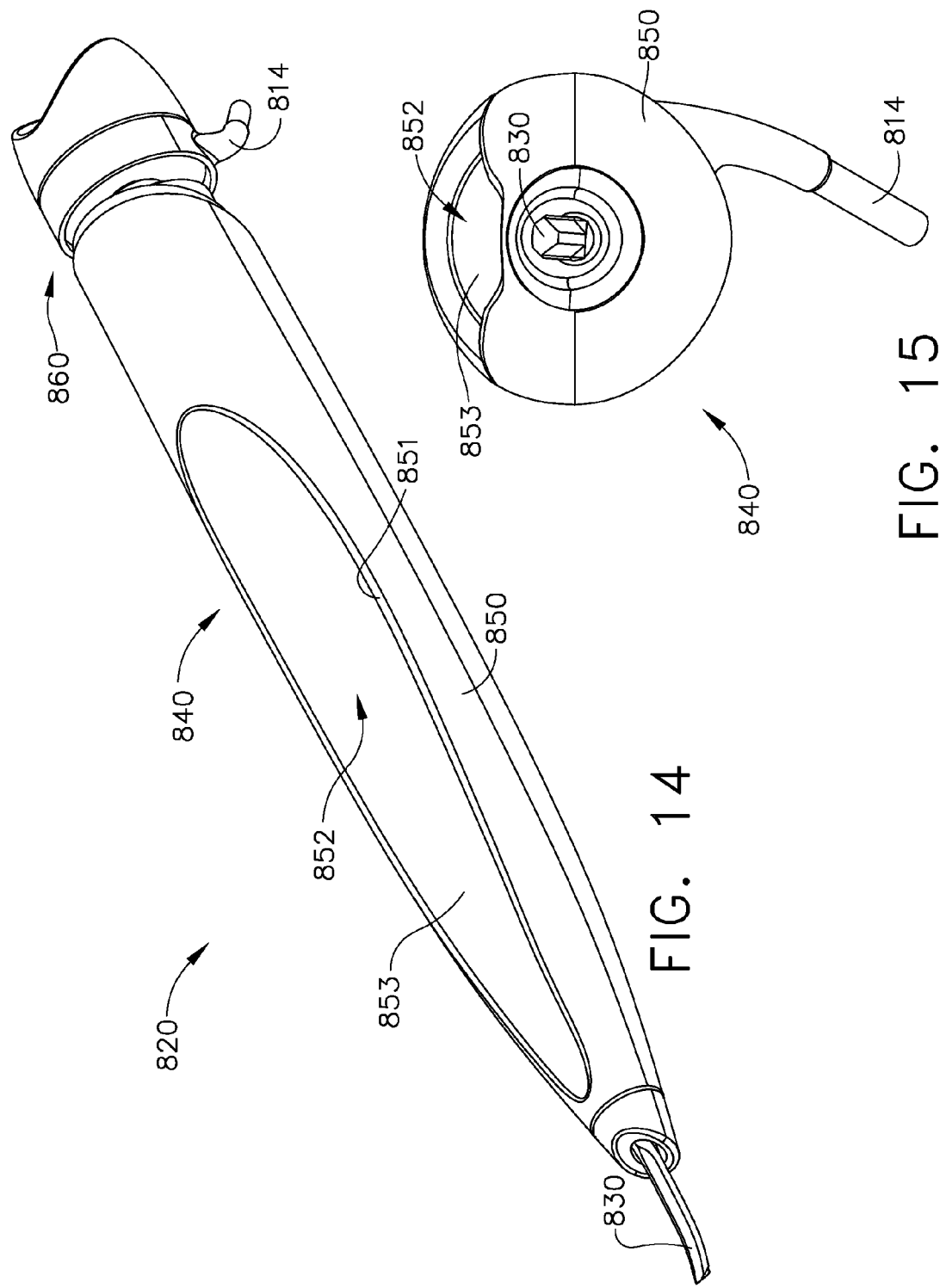
FIG. 14 depicts another perspective view of the ultrasonic surgical device of FIG. 13.
FIG. 15 depicts an end view of the ultrasonic surgical device of FIG. 13.

IX. Exemplary Ultrasonic Surgical Instrument with Rotatable Control and Activation Member FIGS. 13-15 depict another exemplary ultrasonic surgical instrument (820), comprising a blade (830) positioned distally relative to a handpiece (840). An ultrasonic transducer (not shown) is secured in handpiece (840), and may be coupled with an ultrasonic generator (not shown) in accordance with the teachings herein. An ultrasonic waveguide (not shown) couples the ultrasonic transducer with blade (830) in accordance with the teachings herein. It should therefore be understood that an ultrasonic generator may be used to activate the ultrasonic transducer of handpiece (840), and that the activated ultrasonic transducer may transmit ultrasonic vibration to blade (830) via the ultrasonic waveguide in accordance with the teachings herein. Handpiece (840) may be configured to substantially isolate the hand of the user relative to these ultrasonic vibrations. It should also be understood that ultrasonically vibrating blade (830) may be used to perform a variety of surgical procedures. Various other components that may be incorporated into handpiece (840), including but not limited to various components and configurations of electric circuitry, will be apparent to those of ordinary skill in the art in view of the teachings herein.

Instrument (820) of the present example further comprises a housing shell (850), a control member (852), and a tail section (860). Tail section (860) comprises an activation button (862), and has a cable (814) that is coupled with the ultrasonic generator. Housing shell (850), control member (852), and tail section (860) are all independently rotatable relative to each other. That is, housing shell (850) is rotatable relative to control member (852) and tail section (860); control member (852) is rotatable relative to housing shell (850) and tail section (860); and tail section (860) is rotatable relative to housing shell (850) and control member (852). Control member (852) is integrally secured relative to the ultrasonic transducer and relative to blade (830). Thus, when control member (852) is rotated relative to housing shell (850) and/or tail section (860), the ultrasonic transducer and blade (830) rotate unitarily with control member (852). It should be understood that handpiece (840) may include various types of bearings or other features, in various locations, to facilitate the above-described relative rotation while also providing structural support. Furthermore, since tail section (860) (and hence, cable (814)) and control member (852) are rotatable relative to each other, and since control member is unitary with the ultrasonic transducer in this example, slip rings or other components may be included to provide continuous electrical contact despite such relative rotation. In particular, the ultrasonic transducer may be electrically coupled with cable (814) by slip rings or similar components. Similarly, control member (852) may be electrically coupled with cable (814) by slip rings or similar components.

Control member (852) of the present example presents an external surface (853) that may be contacted by the user's hand during use of instrument (840). Housing shell (850) defines an opening (851) that exposes a region of external surface (853), allowing external surface (853) to be contacted by a user's finger or hand. It should be understood that external surface (853) extends about the full circumference of control member (852), such that external surface (853) may be contacted by the user's finger or hand through opening (851) regardless of the rotational position of housing shell (850) relative to control member (852). While the term "circumference" may be used to refer to a dimension of the outer perimeter of control member (852), this should not be read as requiring control member (852) to be cylindrical. While control member (852) may in fact be cylindrical in some versions, control member (852) may alternatively have a variety of other shapes and configurations, including but not limited to tapered or frusto-conical, etc.

Control member (852) is configured such that it is responsive to the location at which the user's hand touches external surface (853). In particular, control member (852) is configured such that the level of ultrasonic energy applied to blade (830) is based at least in part on the longitudinal position at which the user touches external surface (853). For instance, a user touching external surface (853) near the distal end of opening (851) may result in ultrasonic activation of blade (830) at a "maximum" level of ultrasonic energy; while a user touching external surface (853) near the proximal end of opening (851) may result in ultrasonic activation of blade (830) at a "minimum" level of ultrasonic energy. In some versions, control member (852) simply provides selectability between a "minimum" and "maximum" level of ultrasonic energy. In some other versions, control member (852) also provides selectability of ultrasonic energy levels between the "minimum" and "maximum" level, such as when the user touches surface (853) somewhere within the middle region of opening (851). In some such versions, the available energy levels are discrete and predetermined. For instance, as the user moves their hand or finger longitudinally along external surface (853) from the distal end of opening (851) toward the proximal end of opening (851), the ultrasonic energy level may start at the "maximum" level and decrease in stepped increments in accordance with the longitudinal position of the user's hand or finger on external surface (853). Discrete energy levels may thus be associated with discrete longitudinal ranges of length along external surface (853).

In some other versions, the available ultrasonic energy levels may be virtually infinitely variable within a predetermined range. For instance, the ultrasonic energy level may be a substantially linear function of the longitudinal position of the user's hand or finger along the length of external surface (853), such that the ultrasonic energy level progressively and substantially continuously increases or decreases as the user's hand or finger is slid along external surface (853). Still other suitable ways in which the ultrasonic energy level of blade (830) may be based at least in part on the longitudinal position of the user's hand or finger along external surface (853) will be apparent to those of ordinary skill in the art in view of the teachings herein.

It should be understood that various types of technologies may be incorporated into control member (852) to allow it to sense and react to the longitudinal position at which the user's hand touches external surface (853). For instance, control member (852) may comprise a plurality of capacitive switches; a plurality of resistive sensors; resonant cavity switching technology; infrared sensing technology; technology that uses a resonant, standing wave on a surface that is perturbed by the presence of a finger; and/or any other suitable type of technology. In some versions, an array of resistive sensors, infrared sensors, or other types of sensors may be provided in control member (852), to provide substantially continuous sensing of and reaction to the longitudinal position of the user's finger or hand along external surface (853). Control member (852) and associated components may also be configured to discriminate between a user's single finger (e.g., for controlling the energy level for blade (830), etc.) and the hand or multiple fingers of the user (e.g., for activating blade (830) at the selected energy level, etc.). Still other suitable types of and arrangements of switches, sensors, or other technology that may be incorporated into control member (852) will be apparent to those of ordinary skill in the art in view of the teachings herein. Various ways in which such various types of control member (852) components may be incorporated into the circuitry of instrument (820), as well as various circuit components that may accompany or be coupled with variations of control member (852), will also be apparent to those of ordinary skill in the art in view of the teachings herein. By way of example only, a variable resistor and/or some other type(s) of circuit component(s) may be responsive to the longitudinal position of a user's hand or finger along control member (852), and may provide a virtually infinitely variable level of electrical power (within a predefined range) to the ultrasonic transducer in the handpiece (840), which may thereby provide a virtually infinitely variable level of ultrasonic energy (within a predefined range) at blade (830).

Activation button (862) is operable to selectively activate the ultrasonic transducer, to thereby selectively activate blade (830) at the level selected using control member (852). For instance, activation button (862) may act as a switch selectively coupling the ultrasonic transducer with the ultrasonic generator. Activation button (862) may take a variety of forms. By way of example only, activation button (862) may comprise a conventional electromechanical button, a capacitive switch; a resistive sensor; resonant cavity switching technology; infrared sensing technology; technology that uses a resonant, standing wave on a surface that is perturbed by the presence of a finger; and/or any other suitable type of technology. Still other suitable types of switches, sensors, or other technology that may be incorporated into activation button (862) will be apparent to those of ordinary skill in the art in view of the teachings herein. Various ways in which such various types of activation button (862) components may be incorporated into the circuitry of instrument (820), as well as various circuit components that may accompany or be coupled with variations of activation button (862), will also be apparent to those of ordinary skill in the art in view of the teachings herein.

In some other versions of instrument (820), activation button (862) is omitted, such that activation and ultrasonic energy level selection are both provided through control member (852). For instance, instrument (820) may be configured such that as soon as a user touches external surface (853), such touching may simultaneously effect selection of an ultrasonic energy level (e.g., in accordance with the longitudinal position at which external surface (853) is touched) and activation of blade (830). As another merely illustrative example, instrument (820) may be configured such that the role of control member (852) as ultrasonic energy level selector or blade (830) activator is based at least in part on the way in which the user touches external surface (853). For instance, the user may select an ultrasonic energy level by sliding their finger along external surface (853) to a longitudinal position associated with a desired ultrasonic energy level; then activate blade (830) by tapping or double-tapping external surface (853). As another non-limiting example, ultrasonic energy level selection may be based on a number of taps on external surface (853) (e.g., more taps provides higher ultrasonic energy level); while activation of blade (830) is effected through touching external surface (853) for at least a certain duration of time (e.g., three seconds). Alternatively, any other suitable combination of touching external surface (853), sliding against external surface (853), tapping against external surface (853), etc., may be used to provide selection of an ultrasonic energy level and/or activation of blade (830). Such alternatives will be apparent to those of ordinary skill in the art in view of the teachings herein.

As noted above, housing shell (850) and control member (852) are rotatable relative to each other in the present example. As also noted above, control member (852) and blade (830) rotate unitarily with each other in the present example. Therefore, it should be understood that the user may rotate blade (830) relative to housing shell (850) by rotating control member (852) relative to housing shell (850). For instance, the user may use his or her or finger to rotate control member (852) while gripping housing shell (850) with the rest of his or her hand. Housing shell (850) may thus provide a mechanical ground during use of instrument (820), with control member (852) being used to rotate blade (830) to a selected rotational orientation relative to this ground (in addition to control member (852) being used to select a level of ultrasonic energy to be applied to blade (830)). As also noted above, tail section (860) is rotatable relative to both housing shell (850) and control member (852). Furthermore, as shown in FIGS. 13-15, cable (814) extends downwardly from tail section (860). Thus, this rotatability of tail section (860) and the downward orientation of cable (814) may help prevent cable (814) from getting twisted and/or in the way of the user. That is, the rotatability of tail section (860) may help to maintain the downward orientation of cable (814), despite the user's rotation of housing shell (850) and/or control member (852) during use of instrument (820). Furthermore, the use of slip rings (and/or other types of components) may prevent the electrical connections from the ultrasonic transducer (and/or other components) to cable (814) from restricting the degree to which housing shell (850) and/or control member (852) relative to tail section (860).

Handpiece (840) of the present example may be gripped by the user in a variety of ways. By way of example only, a user may grip handpiece (840) like a pencil, with a single hand, with handpiece (840) resting in the crook of the user's hand between the user's thumb and index finger. As another merely illustrative example, the user may grip handpiece (840) with their palm around handpiece (840). It should also be understood that, as noted above, the configuration and rotatability of control member (852) may permit the user to re-orient blade (730) to a selected rotational orientation, while still allowing external surface (853) to be reached and manipulated with relative ease. Of course, any suitable gripping technique may be used.

X. Exemplary Ultrasonic Surgical Instrument with Control and Activation Strip

FIG. 16 depicts another exemplary ultrasonic surgical instrument (920), comprising a blade (930) positioned distally relative to a handpiece (940). An ultrasonic transducer (not shown) is secured in handpiece (940), and may be coupled with an ultrasonic generator (not shown) in accordance with the teachings herein. An ultrasonic waveguide (not shown) is positioned within a sheath (932), which extends distally from handpiece (940). The ultrasonic waveguide couples the ultrasonic transducer with blade (930) in accordance with the teachings herein. It should therefore be understood that an ultrasonic generator may be used to activate the ultrasonic transducer of handpiece (940), and that the activated ultrasonic transducer may transmit ultrasonic vibration to blade (930) via the ultrasonic waveguide in accordance with the teachings herein. Handpiece (940) may be configured to substantially isolate the hand of the user relative to these ultrasonic vibrations. It should also be understood that ultrasonically vibrating blade (930) may be used to perform a variety of surgical procedures. Various other components that may be incorporated into handpiece (940), including but not limited to various components and configurations of electric circuitry, will be apparent to those of ordinary skill in the art in view of the teachings herein.

Instrument (920) of the present example further comprises a control and activation strip (950). Control and activation strip (950) is operable to act as a switch selectively coupling the ultrasonic transducer with the ultrasonic generator. In particular, control and activation strip (950) is operable to simultaneously ultrasonically activate blade (930) and select a desired level of ultrasonic energy to be applied to blade (930). For instance, like control member (852) described above, control and activation strip (950) may control the level of ultrasonic energy applied to blade (930) based at least in part on the longitudinal position at which the user's finger or hand engages control and activation strip (950). For instance, a user touching the distal end of control and activation strip (950) (e.g., the end closest to blade (930)) may result in ultrasonic activation of blade (930) at a "maximum" level of ultrasonic energy; while a user touching the proximal end of control and activation strip (950) (e.g., the end farthest from blade (930)) may result in ultrasonic activation of blade (930) at a "minimum" level of ultrasonic energy.

In some other versions, control and activation strip (950) also provides selectability of ultrasonic energy levels between the "minimum" and "maximum" level, such as when the user touches the longitudinally middle region of control and activation strip (950). In some such versions, the available energy levels are discrete and predetermined. For instance, as the user moves their hand or finger longitudinally along control and activation strip (950), from the distal end of control and activation strip (950) toward the proximal end of control and activation strip (950), the ultrasonic energy level may start at the "maximum" level and decrease in stepped increments in accordance with the longitudinal position of the user's hand or finger on control and activation strip (950). Discrete energy levels may thus be associated with discrete longitudinal ranges of length along control and activation strip (950).

In some other versions, the available ultrasonic energy levels may be virtually infinitely variable within a predetermined range. For instance, the ultrasonic energy level may be a substantially linear function of the longitudinal position of the user's hand or finger along the length of control and activation strip (950), such that the ultrasonic energy level progressively and substantially continuously increases or decreases as the user's hand or finger is slid along control and activation strip (950).

Figure 16A:
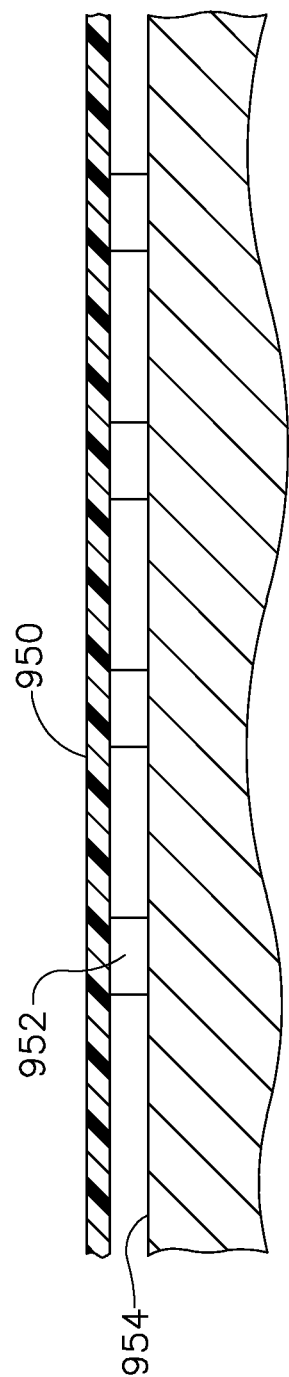
FIG. 16A depicts a partial side cross-sectional view of control and activation components of the ultrasonic surgical device of FIG. 16.

It should be understood that various types of technologies may be incorporated into control and activation strip (950) to allow it to sense and react to the longitudinal position at which the user's hand touches or presses control and activation strip (950). One merely illustrative example is shown in FIG. 16A. As shown, control and activation strip (950) is positioned over a plurality of button switches (952), which are mounted to a substrate (954). In this example, control and activation strip (950) comprises a flexible material (e.g., silicone, rubber, etc.). Button switches (952) may include capacitive switches, thin film switches, electromechanical buttons, or any other type of "button" described herein. Substrate (954) may comprise a printed circuit board having traces that are in communication with button switches (952) and other circuitry of instrument (920). Alternatively, substrate (954) may comprise any other suitable structure having any suitable properties.

In this example, button switches (952) are sized and spaced such that at least one button switch (952) will be actuated when a user presses his or her finger against control and activation strip (950), regardless of where the user presses his or her finger against control and activation strip (950). For instance, some versions of instrument (920) may include eight button switches (952) positioned equidistantly along the length of control and activation strip (950). Alternatively, any other suitable number of buttons switches (952) may be used, in any other suitable arrangement. With having such button switches (952) aligned along the length of control and activation strip (950), button switches (952) may be used to sense the longitudinal position of the user's finger along control and activation strip (950) and communicate with circuitry of instrument (920) accordingly. Various components and configurations of circuitry that may be in communication with button switches (952) will be apparent to those of ordinary skill in the art in view of the teachings herein. Of course, a linear array of button switches (952) is just one example. Similarly, other suitable ways in which the ultrasonic energy level of blade (930) may be based at least in part on the longitudinal position of the user's hand or finger along control and activation strip (950) will be apparent to those of ordinary skill in the art in view of the teachings herein. By way of example only, a variable resistor and/or some other type(s) of circuit component(s) may be responsive to the longitudinal position of the user's hand or finger along control and activation strip (950), and may provide a virtually infinitely variable level of electrical power (within a predefined range) to the ultrasonic transducer in the handpiece (940), which may thereby provide a virtually infinitely variable level of ultrasonic energy (within a predefined range) at blade (930).

In some alternative versions, control and activation strip (950) may comprise a plurality of capacitive switches; a plurality of resistive sensors; resonant cavity switching technology; infrared sensing technology; technology that uses a resonant, standing wave on a surface that is perturbed by the presence of a finger; and/or any other suitable type of technology. Still other suitable types of and arrangements of switches, sensors, or other technology that may be incorporated into control and activation strip (950) will be apparent to those of ordinary skill in the art in view of the teachings herein. Various ways in which such various types of control and activation strip (950) components may be incorporated into the circuitry of instrument (920), as well as various circuit components that may accompany or be coupled with variations of control and activation strip (950), will also be apparent to those of ordinary skill in the art in view of the teachings herein.

As noted above, activation and ultrasonic energy level selection are both provided through control and activation strip (950) in instrument (920) of the present example. For instance, instrument (920) may be configured such that as soon as a user touches control and activation strip (950), such touching may simultaneously effect selection of an ultrasonic energy level (e.g., in accordance with the longitudinal position at which control and activation strip (950) is touched) and activation of blade (930). As another merely illustrative example, instrument (920) may be configured such that the role of control and activation strip (950) as ultrasonic energy level selector or blade (930) activator is based at least in part on the way in which the user touches control and activation strip (950). For instance, the user may select an ultrasonic energy level by sliding their finger along control and activation strip (950) to a longitudinal position associated with a desired ultrasonic energy level; then activate blade (930) by tapping or double-tapping control and activation strip (950). As another non-limiting example, ultrasonic energy level selection may be based on a number of taps on control and activation strip (950) (e.g., more taps provides higher ultrasonic energy level); while activation of blade (930) is effected through touching control and activation strip (950) for at least a certain duration of time (e.g., three seconds). Alternatively, any other suitable combination of touching control and activation strip (950), sliding against control and activation strip (950), tapping against control and activation strip (950), etc., may be used to provide selection of an ultrasonic energy level and/or activation of blade (930). Such alternatives will be apparent to those of ordinary skill in the art in view of the teachings herein. Furthermore, a separate activation button may be provided to activate blade (930), in lieu of or in addition to providing activation of blade (930) via control and activation strip (950).

Handpiece (940) of the present example may be gripped by the user in a variety of ways. By way of example only, a user may grip handpiece (940) like a pencil, with a single hand, with handpiece (940) resting in the crook of the user's hand between the user's thumb and index finger. As another merely illustrative example, the user may grip handpiece (940) with their palm around handpiece (940). It should also be understood that the configuration of control and activation strip (950) may permit the user to rotate the entire handpiece (940) in the user's hand (e.g., about the longitudinal axis defined by handpiece (940)), such as to re-orient blade (930) to a selected rotational orientation, while still allowing control and activation strip (950) to be reached and manipulated with relative ease with handpiece (940) in different rotational orientations. For instance, in some gripping styles of handpiece (940), the user may access and manipulate activation strip (950) using their index finger, middle finger, or other finger. In addition or in the alternative, in some gripping styles of handpiece (940), the user may access and manipulate activation strip (950) using their thumb. Of course, any suitable gripping technique may be used. Furthermore, gripping techniques may be changed or adjusted during a given procedure.

XI. Exemplary Ultrasonic Surgical Instrument with Control and Activation Rings

FIGS. 17-18 depict another exemplary ultrasonic surgical instrument (1020), comprising a blade (1030) positioned distally relative to a handpiece (1040). An ultrasonic transducer (not shown) is secured in handpiece (1040), and may be coupled with an ultrasonic generator (not shown) in accordance with the teachings herein. An ultrasonic waveguide (not shown) is positioned within a sheath (1032), which extends distally from handpiece (1040). The ultrasonic waveguide couples the ultrasonic transducer with blade (1030) in accordance with the teachings herein. It should therefore be understood that an ultrasonic generator may be used to activate the ultrasonic transducer of handpiece (1040), and that the activated ultrasonic transducer may transmit ultrasonic vibration to blade (1030) via the ultrasonic waveguide in accordance with the teachings herein. Handpiece (1040) may be configured to substantially isolate the hand of the user relative to these ultrasonic vibrations. It should also be understood that ultrasonically vibrating blade (1030) may be used to perform a variety of surgical procedures. Various other components that may be incorporated into handpiece (1040), including but not limited to various components and configurations of electric circuitry, will be apparent to those of ordinary skill in the art in view of the teachings herein.

Instrument (1040) of the present example further comprises a distal control and activation ring (1050) and a proximal control and activation ring (1052). Control and activation rings (1050, 1052) are each configured to act as a switch selectively coupling the ultrasonic transducer with the ultrasonic generator. In particular, control and activation rings (1050, 1052) are operable to simultaneously ultrasonically activate blade (1030) and select a desired level of ultrasonic energy to be applied to blade (1030). For instance, distal control and activation ring (1050) may be "actuated" to simultaneously select a "maximum" level of ultrasonic energy and ultrasonically activate blade (1030) with the selected "maximum" level of ultrasonic energy; while proximal control and activation ring (1052) may be "actuated" to simultaneously select a "minimum" level of ultrasonic energy and ultrasonically activate blade (1030) with the selected "minimum" level of ultrasonic energy. Alternatively, these roles may be reversed. It should also be understood that additional control and activation rings may be included to provide more than two ultrasonic energy levels to choose from.

In some versions, control and activation rings (1050, 1052) are each independently slidable along the longitudinal axis defined by handpiece (1040) to "actuate" a selected control and activation ring (1050, 1052). For instance, distal control and activation ring (1050) may be slid distally to activate blade (1030) with a "maximum" level of ultrasonic energy; while proximal control and activation ring (1050) may be slid proximally to activate blade (1030) with a "minimum" level of ultrasonic energy. Blade (1030) may remain inactive when control and activation rings (1050, 1052) are both in a default or non-slid position. Detent features or other features may provide some degree of resistance to sliding of control and activation rings (1050, 1052) when control and activation rings (1050, 1052) are in the default position. Similarly, regardless of which control and activation ring (1050, 1052) is slid from its default position, detent features or other features may provide some degree of resistance to sliding of a control and activation ring (1050, 1052) when the control and activation ring (1050, 1052) is in a slid position. In some versions, when both of control and activation rings (1050, 1052) are in a slid position, blade (1030) may be activated at a "medium" level of ultrasonic energy. Of course, the foregoing configuration and operability is merely optional.

In some other versions, control and activation rings (1050, 1052) do not slide at all. For instance, control and activation rings (1050, 1052) may comprise capacitive switches; resistive sensors; resonant cavity switching technology; infrared sensing technology; technology that uses a resonant, standing wave on a surface that is perturbed by the presence of a finger; and/or any other suitable type of technology. Control and activation rings (1050, 1052) may thus be "actuated" simply by touching or pressing on a selected one of control and activation rings (1050, 1052). As another merely illustrative example, control and activation rings (1050, 1052) may be configured in accordance with the teachings of U.S. Pub. No. 2007/0191713, entitled "Ultrasonic Device for Cutting and Coagulating," published Aug. 16, 2007, the disclosure of which is incorporated by reference herein. Still other suitable types of switches, sensors, or other technology that may be incorporated into control and activation rings (1050, 1052) will be apparent to those of ordinary skill in the art in view of the teachings herein. Similarly, various ways in which such various types of control and activation ring (1050, 1052) components may be incorporated into the circuitry of instrument (1020), as well as various circuit components that may accompany or be coupled with variations of control and activation rings (1050, 1052), will be apparent to those of ordinary skill in the art in view of the teachings herein. Furthermore, some versions of handpiece (1040) may have just one activation ring (1050 or 1052) instead of having two activation rings (1050, 1052).

Handpiece (1040) of the present example may be gripped by the user in a variety of ways. By way of example only, a user may grip handpiece (1040) like a pencil, with a single hand, with handpiece (1040) resting in the crook of the user's hand between the user's thumb and index finger. As another merely illustrative example, the user may grip handpiece (1040) with their palm around handpiece (1040). It should also be understood that the configuration of control and activation rings (1050, 1052) may permit the user to rotate the entire handpiece (1040) in the user's hand (e.g., about the longitudinal axis defined by handpiece (1040)), such as to re-orient blade (1030) to a selected rotational orientation, while still allowing control and activation rings (1050, 1052) to be reached and manipulated with relative ease with handpiece (1040) in different rotational orientations. In other words, control and activation rings (1050, 1052) of the present example are accessible from any angular position within a 360° range about the axis defined by handpiece (1040). Of course, any suitable gripping technique may be used.

XII. Exemplary Ultrasonic Surgical Instrument with Crushable Cage

Figure 19:
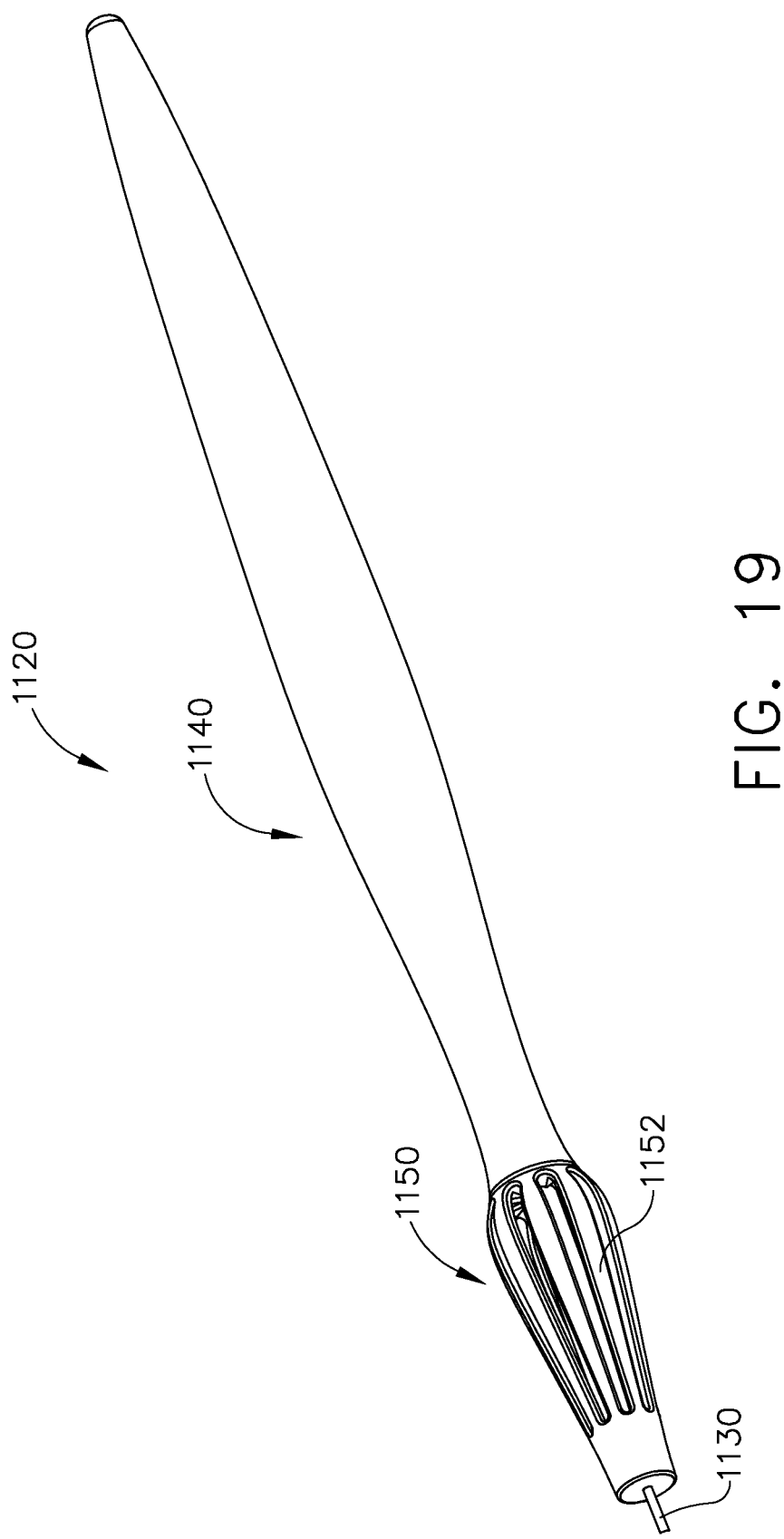
FIG. 19 depicts a perspective view of another exemplary ultrasonic surgical device, having a crushable cage.

FIG. 19 depicts another exemplary ultrasonic surgical instrument (1120), comprising a blade (1130) positioned distally relative to a handpiece (1140). Blade (1130) is shown in FIG. 19 in schematic form, it being understood that blade (1130) may be significantly further spaced from handpiece (1140) in some versions of instrument (1120). An ultrasonic transducer (not shown) is secured in handpiece (1140), and may be coupled with an ultrasonic generator (not shown) in accordance with the teachings herein. An ultrasonic waveguide (not shown) couples the ultrasonic transducer with blade (1130) in accordance with the teachings herein. It should therefore be understood that an ultrasonic generator may be used to activate the ultrasonic transducer of handpiece (1140), and that the activated ultrasonic transducer may transmit ultrasonic vibration to blade (1130) via the ultrasonic waveguide in accordance with the teachings herein. Handpiece (1140) may be configured to substantially isolate the hand of the user relative to these ultrasonic vibrations. It should also be understood that ultrasonically vibrating blade (1130) may be used to perform a variety of surgical procedures. Various other components that may be incorporated into handpiece (1140), including but not limited to various components and configurations of electric circuitry, will be apparent to those of ordinary skill in the art in view of the teachings herein.

Instrument (1020) of the present example further comprises a crushable cage (1150). Crushable cage (1150) is positioned about a control and activation rod (not shown), which extends longitudinally through the interior of crushable cage (1150) and which is operable to act as a switch selectively coupling the ultrasonic transducer with the ultrasonic generator. In particular, the control and activation rod is operable to simultaneously ultrasonically activate blade (1130) and select a desired level of ultrasonic energy to be applied to blade (1130). For instance, like control member (852) described above, the control and activation rod may control the level of ultrasonic energy applied to blade (1130) based at least in part on the longitudinal position at which the control and activation rod is engaged. For instance, engaging the distal end of the control and activation rod (e.g., the end closest to blade (1130)) may result in ultrasonic activation of blade (1130) at a "maximum" level of ultrasonic energy; while engaging the proximal end of the control and activation rod (e.g., the end farthest from blade (930)) may result in ultrasonic activation of blade (1130) at a "minimum" level of ultrasonic energy.

The control and activation rod may comprise any of a variety of components or features to provide the above-described operability. By way of example only, two or more buttons may be located along the length of the control and activation rod and/or about the circumference of the control and activation rod. Such buttons may comprise thin film switches, electromechanical buttons, or any other type of "button" described herein such as capacitive switches; resistive sensors; resonant cavity switching technology; infrared sensing technology; technology that uses a resonant, standing wave on a surface that is perturbed by the presence of a finger; and/or any other suitable type of technology. Still other suitable types of and arrangements of switches, sensors, or other technology that may be incorporated into a control and activation rod will be apparent to those of ordinary skill in the art in view of the teachings herein. Various ways in which such various types of control and activation rod components may be incorporated into the circuitry of instrument (1120), as well as various circuit components that may accompany or be coupled with variations of a control and activation rod, will also be apparent to those of ordinary skill in the art in view of the teachings herein.

Crushable cage (1150) of the present example comprises a plurality of crushable ribs (1152), which extend longitudinally and bow outwardly about the control and activation rod. Ribs (1152) are flexible, and are resiliently biased to the outwardly bowed configuration shown in FIG. 19. For instance, ribs (1152) may be formed of a resilient plastic or any other suitable material or combination of materials. Crushable cage (1150) is configured such that at least some of ribs (1152) must be flexed inwardly in order for the user to sufficiently engage the control and activation rod to activate blade (1130). In other words, the control and activation rod will be non-engaged, and hence the blade (1130) non-activated, when ribs (1152) are in the outwardly bowed configuration shown in FIG. 19. Crushable cage (1150) may thus reduce the likelihood of inadvertent activation of blade (1130).

Ribs (1152) may be forced inwardly, thereby crushing or collapsing cage (1150), by a user pinching cage (1150) with their thumb and/or fingers. As ribs (1152) are forced inwardly, ribs (1152) may approach the control and activation rod with sufficient proximity to engage the control and activation rod. In versions where the control and activation rod comprises capacitive switches (among other versions), ribs (1152) necessarily touch the control and activation rod in order to sufficiently engage the rod to activate blade (1130). In some other versions, instrument (1140) may require ribs (1152) to actually touch the control and activation rod (or some component(s) thereof) in order to sufficiently engage the rod to activate blade (1130). As noted above, the ultrasonic energy level delivered to blade (1130) may be based at least in part on the longitudinal position at which the control and activation rod is engaged. Thus, the ultrasonic energy level delivered to blade (1130) may be based at least in part on the longitudinal position at which ribs (1152) are forced inwardly. The variability of the ultrasonic energy level delivered to blade may be in discrete increments or may be substantially continuous, as described herein.

In some versions of instrument (1120), the interior of ribs (1152) is electrically conductive, and they must contact a complementary electrically conductive surface on the control and activation rod in order to activate blade (1130). In still other versions, the control and activation rod is omitted entirely. For instance, ribs (1152) may include strain gauges, which may act as switches that are sensitive to crushing or collapsing of cage (1150) by the user in order to activate blade (1130). Other suitable variations, components, features, and operability of cage (1150) will be apparent to those of ordinary skill in the art in view of the teachings herein.

Handpiece (1140) of the present example may be gripped by the user in a variety of ways. By way of example only, a user may grip handpiece (1140) like a pencil, with a single hand, with handpiece (1140) resting in the crook of the user's hand between the user's thumb and index finger. As another merely illustrative example, the user may grip handpiece (1140) with their palm around handpiece (1140). It should also be understood that the configuration of cage (1150) may permit the user to rotate the entire handpiece (1140) in the user's hand (e.g., about the longitudinal axis defined by handpiece (1140)), such as to re-orient blade (1130) to a selected rotational orientation, while still allowing cage (1150) to be reached and manipulated with relative ease with handpiece (1140) in different rotational orientations. Of course, any suitable gripping technique may be used.

XIII. Exemplary Ultrasonic Surgical Instrument with Angularly Arrayed Buttons

Figure 20:
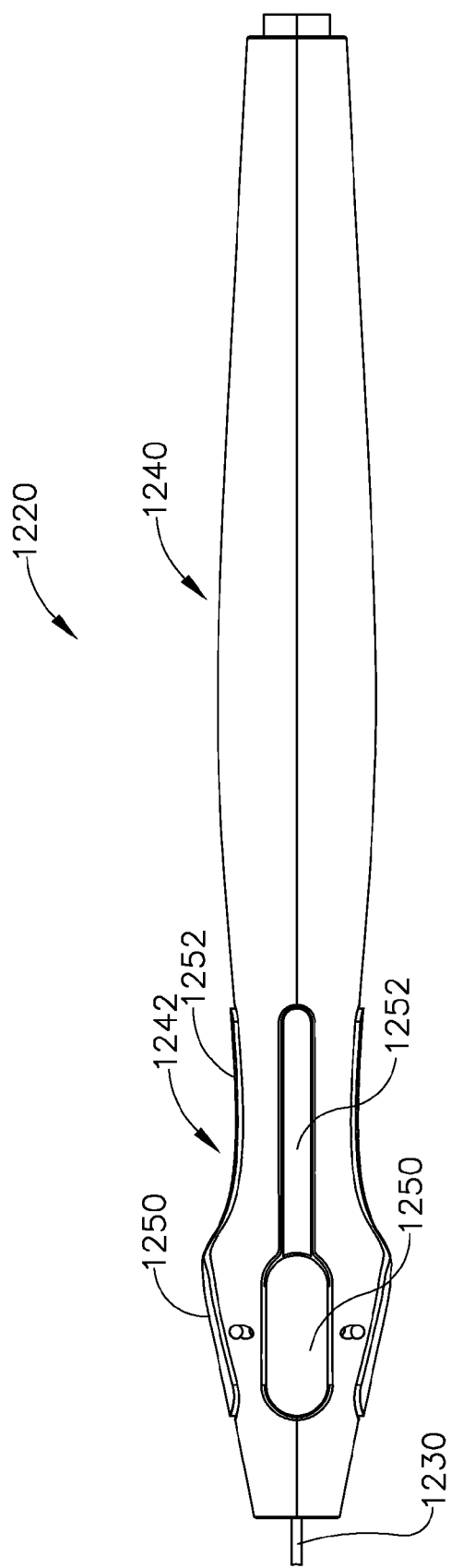
FIG. 20 depicts an elevational view of another exemplary ultrasonic surgical device, having multiple power mode selection switches and multiple activation switches.

FIG. 20 depicts another exemplary ultrasonic surgical instrument (1220), comprising a blade (1230) positioned distally relative to a handpiece (1240). Blade (1230) is shown in FIG. 20 in schematic form, it being understood that blade (1230) may be significantly further spaced from handpiece (1240) in some versions of instrument (1220). An ultrasonic transducer (not shown) is secured in handpiece (1240), and may be coupled with an ultrasonic generator (not shown) in accordance with the teachings herein. An ultrasonic waveguide (not shown) couples the ultrasonic transducer with blade (1230) in accordance with the teachings herein. It should therefore be understood that an ultrasonic generator may be used to activate the ultrasonic transducer of handpiece (1240), and that the activated ultrasonic transducer may transmit ultrasonic vibration to blade (1230) via the ultrasonic waveguide in accordance with the teachings herein. Handpiece (1240) may be configured to substantially isolate the hand of the user relative to these ultrasonic vibrations. It should also be understood that ultrasonically vibrating blade (1230) may be used to perform a variety of surgical procedures. Various other components that may be incorporated into handpiece (1240), including but not limited to various components and configurations of electric circuitry, will be apparent to those of ordinary skill in the art in view of the teachings herein.

Instrument (1220) of the present example further comprises control buttons (1250) and activation buttons (1252). Control buttons (1250) and activation buttons (1252) are provided in pairs, with the control button (1250) of each pair being position distal to the associated activation button (1252) of the pair. Of course, this relationship could be reversed or otherwise changed. In addition, the pairs of buttons (1250, 1252) are angularly arrayed about the longitudinal axis defined by handpiece (1240) in increments of 90°. Accordingly, instrument (1020) has four pairs of buttons (1250, 1252). Of course, instrument (1020) may have any other suitable number of pairs of buttons (1250, 1252). Similarly, pairs of buttons (1250, 1252) may be provided in any other suitable arrangement, including but not limited to alternative angular arrays. Some versions of instrument (1020) may also include a number of control buttons (1250) that differs from the number of activation buttons (1252) (e.g., one control button (1250) and four activation buttons (1252), etc.). Other suitable configurations and arrangements of buttons (1250, 1252) will be apparent to those of ordinary skill in the art in view of the teachings herein. The following description will refer to each type of button (1250, 1252) in the singular form, it being understood that the description may apply to all corresponding buttons (1250, 1252) of instrument (1220).

Control button (1250) of this example comprises a domed switch that may be tapped to change power modes, to thereby select a desired level of ultrasonic energy to be applied to blade (1230). In particular, control button (1250) may be tapped to cycle between a "maximum" level of ultrasonic energy and a "minimum" level of ultrasonic energy. While control selector (250) provides selection from only two levels in this example, it should be understood that control selector (1250) may provide selection of any other suitable number of levels. Furthermore, various ways in which manipulation of control selector (1250) may affect electrical power provided to the ultrasonic transducer will be apparent to those of ordinary skill in the art in view of the teachings herein. By way of example only, instrument (1220) may include circuitry similar to that described above and shown in FIG. 2. Other suitable circuitry that may be in communication with control selector (1250) will be apparent to those of ordinary skill in the art in view of the teachings herein.

Activation button (1252) is operable to selectively activate the ultrasonic transducer, to thereby selectively activate blade (1230). For instance, activation button (1252) may act as a switch selectively coupling the ultrasonic transducer with the ultrasonic generator. In some versions, just one activation button (1252) needs to be actuated in order to activate blade (1230). In some other versions, at least two activation buttons (1252) need to be actuated at the same time in order to activate blade (1230). In the present example, handpiece (1240) is configured such that activation buttons (1252) lie in a circumferentially extending valley (1242), which may reduce the likelihood of activation buttons (1252) being inadvertently actuated. Of course, valley (1242) is merely optional, and handpiece (1240) may have any other suitable configuration.

Activation button (1252) may take a variety of forms. By way of example only, activation button (1252) may comprise a conventional electromechanical button, a capacitive switch; a resistive sensor; resonant cavity switching technology; infrared sensing technology; technology that uses a resonant, standing wave on a surface that is perturbed by the presence of a finger; and/or any other suitable type of technology. Of course, control button (1250) may also take any such alternative forms. Still other suitable types of switches, sensors, or other technology that may be incorporated into activation button (1252) or control button (1250) will be apparent to those of ordinary skill in the art in view of the teachings herein. Various ways in which such various types of activation button (1252) and control button (1250) components may be incorporated into the circuitry of instrument (1220), as well as various circuit components that may accompany or be coupled with variations of activation button (1252) and control button (1250), will be apparent to those of ordinary skill in the art in view of the teachings herein.

Handpiece (1240) of the present example may be gripped by the user in a variety of ways. By way of example only, a user may grip handpiece (1240) like a pencil, with a single hand, with handpiece (1240) resting in the crook of the user's hand between the user's thumb and index finger. As another merely illustrative example, the user may grip handpiece (1240) with their palm around handpiece (1240). It should also be understood that the configuration and arrangement of buttons (1250, 1252) may permit the user to rotate the entire handpiece (1240) in the user's hand (e.g., about the longitudinal axis defined by handpiece (1240)), such as to re-orient blade (1230) to a selected rotational orientation, while still allowing at least one pair of buttons (1250, 1252) to be reached and manipulated with relative ease with handpiece (1240) in different rotational orientations. Of course, any suitable gripping technique may be used.

XIV. Exemplary Ultrasonic Surgical Instrument with Angularly Arrayed Ribs

FIGS. 21-22 depict another exemplary ultrasonic surgical instrument (1320), comprising a blade (1330) positioned distally relative to a handpiece (1340). An ultrasonic transducer (not shown) is secured in handpiece (1340), and may be coupled with an ultrasonic generator (not shown) in accordance with the teachings herein. An ultrasonic waveguide (not shown) is positioned within a sheath (1332), which extends distally from handpiece (1340). The ultrasonic waveguide couples the ultrasonic transducer with blade (1330) in accordance with the teachings herein. It should therefore be understood that an ultrasonic generator may be used to activate the ultrasonic transducer of handpiece (1340), and that the activated ultrasonic transducer may transmit ultrasonic vibration to blade (1330) via the ultrasonic waveguide in accordance with the teachings herein. Handpiece (1340) may be configured to substantially isolate the hand of the user relative to these ultrasonic vibrations. It should also be understood that ultrasonically vibrating blade (1330) may be used to perform a variety of surgical procedures. Various other components that may be incorporated into handpiece (1340), including but not limited to various components and configurations of electric circuitry, will be apparent to those of ordinary skill in the art in view of the teachings herein.

Instrument (1320) of the present example further comprises a three control and activation ribs (1350). Control and activation ribs (1350) are angularly arrayed about the longitudinal axis defined by handpiece (1340) in increments of 120°. Of course, instrument (1320) may have any other suitable number of control and activation ribs (1350). Similarly, control and activation ribs (1350) may be provided in any other suitable arrangement, including but not limited to alternative angular arrays. Other suitable configurations and arrangements of control and activation ribs (1350) will be apparent to those of ordinary skill in the art in view of the teachings herein. The following description will refer to control and activation ribs (1350) in the singular form, it being understood that the description may apply to all control and activation ribs (1350) of instrument (1320).

Control and activation rib (1350) is operable to act as a switch selectively coupling the ultrasonic transducer with the ultrasonic generator. In particular, control and activation rib (1350) is operable to simultaneously ultrasonically activate blade (1330) and select a desired level of ultrasonic energy to be applied to blade (1330). For instance, as with control and activation strip (950) described above, control and activation rib (1350) may control the level of ultrasonic energy applied to blade (1330) based at least in part on the longitudinal position at which the user's finger or hand engages control and activation rib (1350). Indeed, any or all of the teachings above with respect to activation strip (950) (including but not limited to features, operability, variations, etc.) may be readily applied to each activation rib (1350). Still other suitable types of and arrangements of switches, sensors, or other technology that may be incorporated into control and activation rib (1350) will be apparent to those of ordinary skill in the art in view of the teachings herein. Various ways in which such various types of control and activation rib (1350) components may be incorporated into the circuitry of instrument (1320), as well as various circuit components that may accompany or be coupled with variations of control and activation rib (1350), will also be apparent to those of ordinary skill in the art in view of the teachings herein.

In some versions, the user must actuate at least two control and activation ribs (1350) simultaneously in order to activate blade (1330). Alternatively, any other suitable method or combination of touching control and activation rib (1350), sliding against control and activation rib (1350), tapping against control and activation rib (1350), etc., may be used to provide selection of an ultrasonic energy level and/or activation of blade (1330). Such alternatives will be apparent to those of ordinary skill in the art in view of the teachings herein. Furthermore, a separate activation button may be provided to activate blade (1330), in lieu of or in addition to providing activation of blade (1330) via control and activation rib (1350).

Handpiece (1340) of the present example may be gripped by the user in a variety of ways. By way of example only, a user may grip handpiece (1340) like a pencil, with a single hand, with handpiece (1340) resting in the crook of the user's hand between the user's thumb and index finger. As another merely illustrative example, the user may grip handpiece (1340) with their palm around handpiece (1340). It should also be understood that the configuration and arrangement of control and activation ribs (1350) may permit the user to rotate the entire handpiece (1340) in the user's hand (e.g., about the longitudinal axis defined by handpiece (1340)), such as to re-orient blade (1330) to a selected rotational orientation, while still allowing at least one control and activation rib (1350) to be reached and manipulated with relative ease with handpiece (1340) in different rotational orientations. Of course, any suitable gripping technique may be used.

Figure 23:
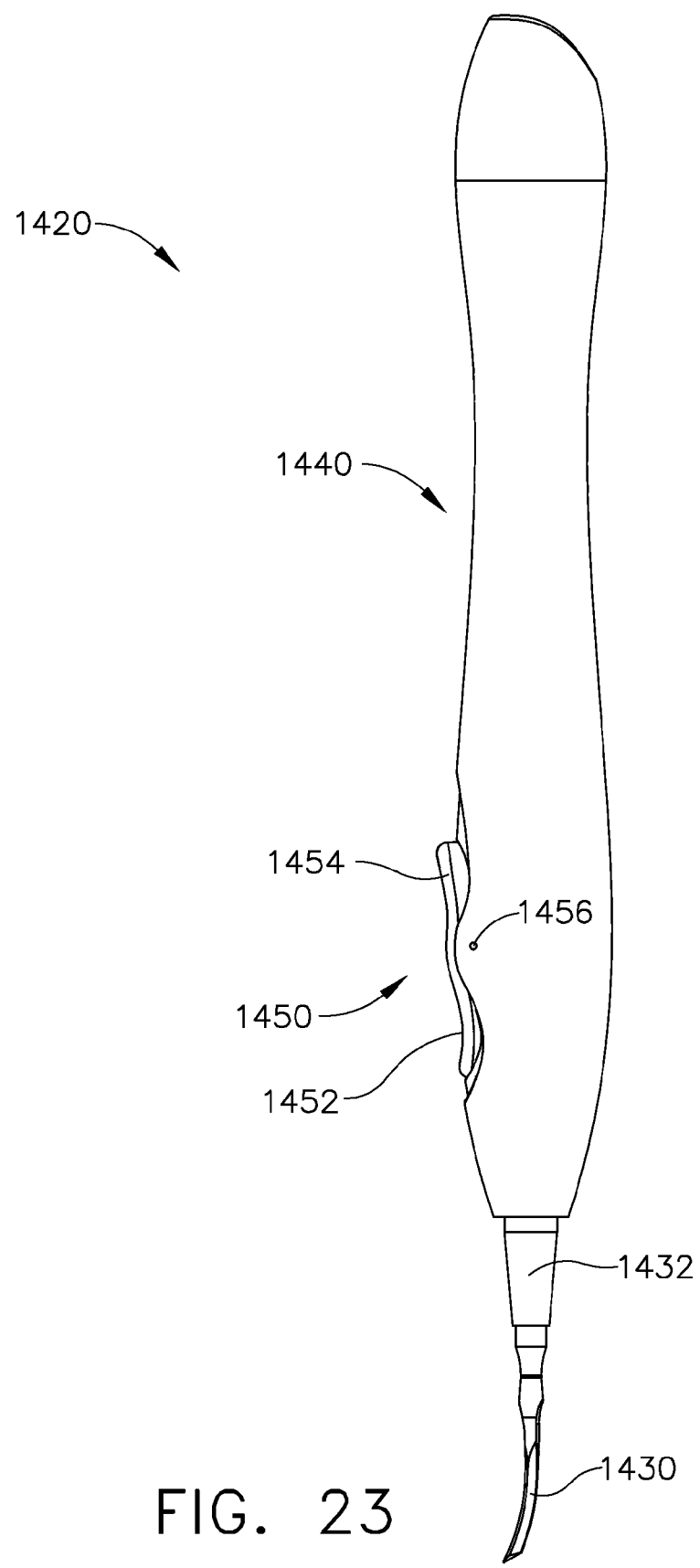
FIG. 23 depicts an elevational view of another exemplary ultrasonic surgical device, having a rocker control switch.

XV. Exemplary Ultrasonic Surgical Instrument with Rocking Control and Activation Button FIG. 23 depicts another exemplary ultrasonic surgical instrument (1420), comprising a blade (1430) positioned distally relative to a handpiece (1440). An ultrasonic transducer (not shown) is secured in handpiece (1440), and may be coupled with an ultrasonic generator (not shown) in accordance with the teachings herein. An ultrasonic waveguide (not shown) is positioned within a sheath (1432), which extends distally from handpiece (1440). The ultrasonic waveguide couples the ultrasonic transducer with blade (1430) in accordance with the teachings herein. It should therefore be understood that an ultrasonic generator may be used to activate the ultrasonic transducer of handpiece (1440), and that the activated ultrasonic transducer may transmit ultrasonic vibration to blade (1430) via the ultrasonic waveguide in accordance with the teachings herein. Handpiece (1440) may be configured to substantially isolate the hand of the user relative to these ultrasonic vibrations. It should also be understood that ultrasonically vibrating blade (1430) may be used to perform a variety of surgical procedures. Various other components that may be incorporated into handpiece (1440), including but not limited to various components and configurations of electric circuitry, will be apparent to those of ordinary skill in the art in view of the teachings herein.

Instrument (1420) of the present example further comprises a rocker switch (1450). Rocker switch (1450) includes a distal portion (1452) and a proximal portion (1454), and is operable to rock about a pin (1456) that secures rocker switch (1450) to handpiece (1440). In some versions, distal portion (1452) has a concave configuration while proximal portion (1454) has a convex configuration. Such configurations may allow a user to easily and differentiate between distal portion (1452) and a proximal portion (1454) by sense of touch alone. Rocker switch (1450) is operable to act as a switch selectively coupling the ultrasonic transducer with the ultrasonic generator. In particular, rocker switch (1450) is operable to simultaneously ultrasonically activate blade (1430) and select a desired level of ultrasonic energy to be applied to blade (1430). For instance, by pressing on distal portion (1452), the user may activate blade (1430) at a "maximum" level of ultrasonic energy. By pressing on proximal portion (1454), the user may activate blade (1430) at a "minimum" level of ultrasonic energy. Of course, these roles may be reversed. In either case, it should be understood that the user may simply slide their finger along rocker switch (1450) to toggle between "maximum" and "minimum" levels of ultrasonic energy. Various ways in which various types of rocker switch (1450) components may be incorporated into the circuitry of instrument (1420), as well as various circuit components that may accompany or be coupled with variations of rocker switch (1450), will be apparent to those of ordinary skill in the art in view of the teachings herein.

In some versions, rocker switch (1450) includes a detent or other feature that provides a clicking sound and/or some form of haptic feedback to the user when either distal portion (1452) or proximal portion (1454) has been sufficiently depressed, providing confirmation to the user that blade (1430) has been activated. It should also be understood that, in some versions, and compared to versions using dome switches or certain other types of switches, the mechanical advantage and increased arc of travel for rocker switch (1450) may decrease the likelihood of inadvertent activation and/or allow minimization of the finger pressure that is needed to activate the switch. Such a reduction of finger pressure may translate into reduced finger fatigue for the user, particularly in procedures where instrument (1420) is used for several hours; and may also provide more dexterous handling of instrument (1420).

Handpiece (1440) of the present example may be gripped in any suitable fashion, including but not limited to using any of the gripping techniques described herein. Of course, any suitable gripping technique may be used.

XVI. Exemplary Ultrasonic Surgical Instrument with Broad Proximal End

Figure 24:
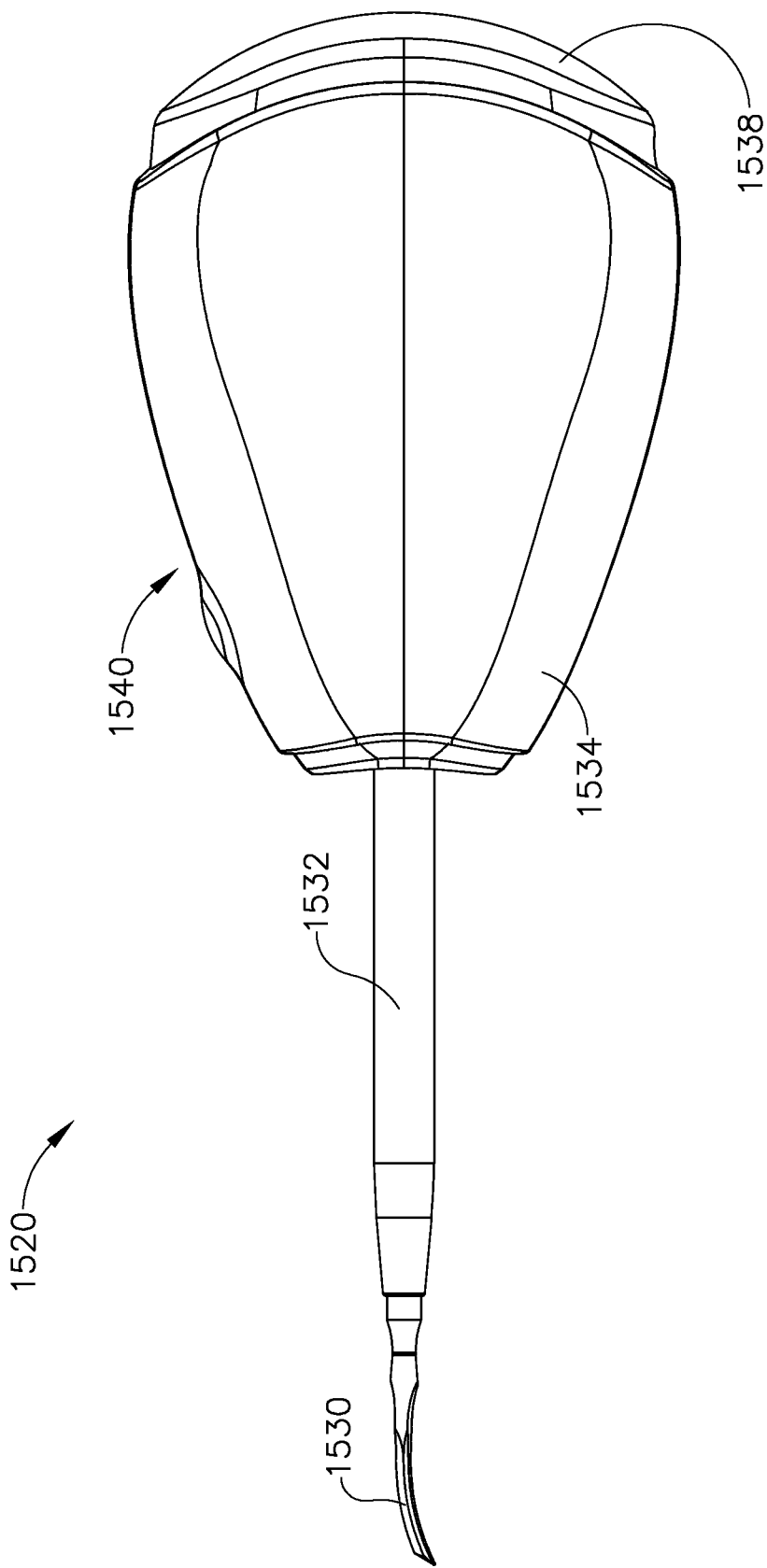
FIG. 24 depicts an elevational view of another exemplary ultrasonic surgical device, having a wedge-shaped handpiece.
Figure 25:
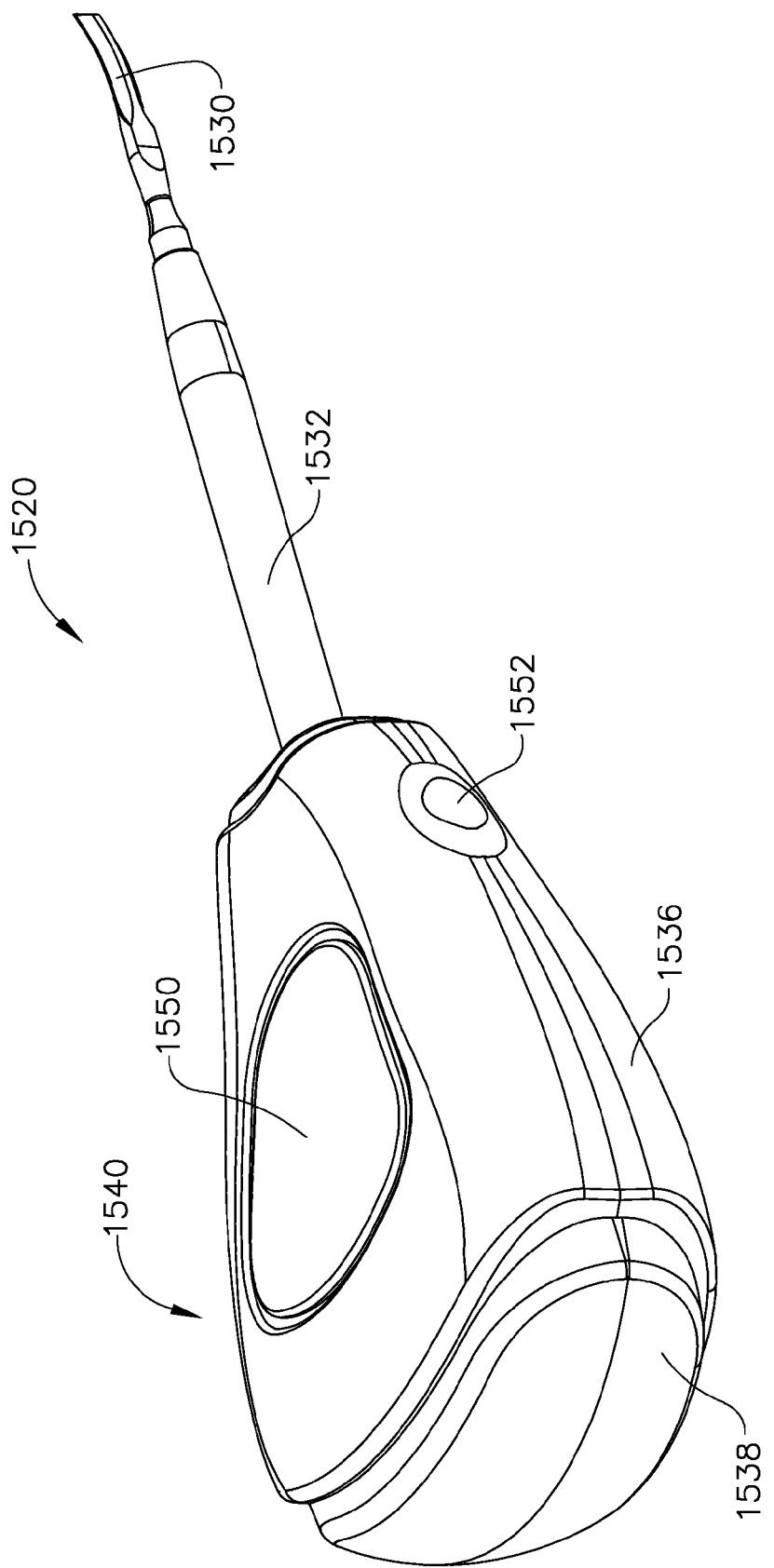
FIG. 25 depicts a perspective view of the ultrasonic surgical device of FIG. 24, with an outer sheath removed.

FIGS. 24-25 depict another exemplary ultrasonic surgical instrument (1520), comprising a blade (1530) positioned distally relative to a handpiece (1540). An ultrasonic transducer (not shown) is secured in handpiece (1540), and may be coupled with an ultrasonic generator (not shown) in accordance with the teachings herein. An ultrasonic waveguide (not shown) is positioned within a sheath (1532), which extends distally from handpiece (1540). The ultrasonic waveguide couples the ultrasonic transducer with blade (1530) in accordance with the teachings herein. It should therefore be understood that an ultrasonic generator may be used to activate the ultrasonic transducer of handpiece (1540), and that the activated ultrasonic transducer may transmit ultrasonic vibration to blade (1530) via the ultrasonic waveguide in accordance with the teachings herein. Handpiece (1540) may be configured to substantially isolate the hand of the user relative to these ultrasonic vibrations. It should also be understood that ultrasonically vibrating blade (1530) may be used to perform a variety of surgical procedures. Various other components that may be incorporated into handpiece (1540), including but not limited to various components and configurations of electric circuitry, will be apparent to those of ordinary skill in the art in view of the teachings herein.

Handpiece (1540) of the present example comprises an elastomeric sheath (1534) positioned over a rigid housing (1536). As shown in FIG. 25, housing (1536) includes a broad proximal end (1538). As also shown in FIG. 25, handpiece (1540) comprises side buttons (1550) and edge buttons (1552). While only one side button (1550) is shown in FIG. 25, it should be understood that an identical side button (1550) is on the opposite side of housing (1536) in the present example. Similarly, while only one edge button (1552) is shown in FIG. 25, it should be understood that an identical edge button (1552) is on the opposite side of housing (1536) in the present example. Of course, handpiece (1540) may alternatively comprise only one of each type of button (1550, 1552) or any other suitable configuration of buttons. Elastomeric sheath (1534) of the present example fits over rigid housing (1536), covering buttons (1550, 1552), but leaving broad proximal end (1538) exposed. Elastomeric properties of sheath (1534) facilitate gripping of handpiece (1540) while not significantly inhibiting actuation of buttons (1550, 1552).

Each button (1550, 1552) is operable to act as a switch selectively coupling the ultrasonic transducer with the ultrasonic generator. In particular, each button (1550, 1552) is operable to simultaneously ultrasonically activate blade (1530) and select a desired level of ultrasonic energy to be applied to blade (1530). For instance, by pressing on either side button (1550), the user may activate blade (1530) at a "maximum" level of ultrasonic energy. By pressing on either edge button (1552), the user may activate blade (1530) at a "minimum" level of ultrasonic energy. Of course, these roles may be reversed. Various ways in which various types of button (1550, 1552) components may be incorporated into the circuitry of instrument (1520), as well as various circuit components that may accompany or be coupled with variations of buttons (1550, 1552), will be apparent to those of ordinary skill in the art in view of the teachings herein.

Figure 26:
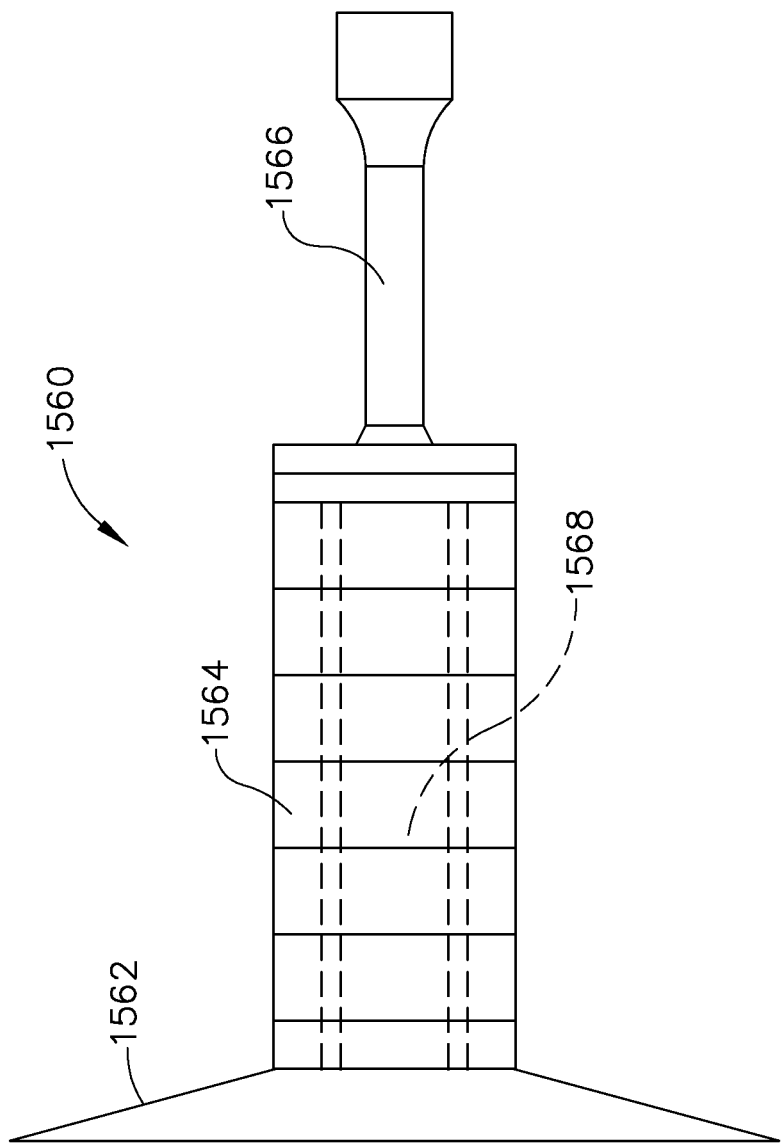
FIG. 26 depicts a side view of the ultrasonic transducer of the ultrasonic surgical device of FIG. 24.

In some versions, instrument (1520) comprises a conventional ultrasonic transducer. In some other versions, instrument (1520) comprises the ultrasonic transducer (1560) shown in FIG. 26. Ultrasonic transducer (1560) of this example is a 55 Khz half wave transducer, and comprises an endmass (1562), a plurality of piezo discs (1564), a horn (1566), and a bolt (1568) joining these components together. In the present example, endmass (1562) comprises tungsten, has a frusto-conical shape, and has a maximum diameter of approximately 32 mm. Alternatively, any other suitable material(s) and/or shapes and/or dimensions may be used. While ultrasonic transducer (1560) has six piezo discs (1564), it should be understood that any other suitable number of piezo discs (1564) may be used. Also in the present example, piezo discs (1564) comprise lead zirconate titanate (PZT), and each piezo disc (1564) has an outer diameter of approximately 10 mm. Again, though, any other suitable material(s) and/or dimensions may be used. As will be apparent to those of ordinary skill in the art, piezo discs (1564) are configured to convert electrical energy into ultrasonic vibrational energy. Horn (1566) and bolt (1568) of the present example are formed of Ti64, though it should be understood that any other suitable material(s) may be used.

Ultrasonic transducer (1560) of the present example has an overall length of approximately 33 mm. Such a length may represent the halfwave, where the full resonant wavelength of ultrasonic transducer (1560) is 66 mm. Alternatively, ultrasonic transducer (1560) may have any other suitable length. By way of example only, including but not limited to versions where the full resonant wavelength of ultrasonic transducer (1560) is 66 mm, ultrasonic transducer (1560) may have a length that is any factor of 33 mm. The electrical energy is provided to endmass (1562) from the generator. This excites the piezo discs (1564) to produce the ultrasonic vibrational energy, which is communicated to horn (1566). Horn (1566) acoustically amplifies the ultrasonic wave, in the sense that its "necking down" configuration provides acoustic gain. Horn (1566) is coupled with the ultrasonic waveguide, which transmits the vibrational energy to blade (1530). Of course, ultrasonic transducer (1560) may work in any other suitable fashion, may have ant other suitable components and/or configurations; and any other suitable ultrasonic transducer may be used.

Handpiece (1540) of the present example may be gripped by the user in a variety of ways. By way of example only, a user may grip handpiece (1540) like a pencil, with a single hand, with handpiece (1540) resting in the crook of the user's hand between the user's thumb and index finger. In some settings, such a grip may be preferred to perform "fine" work with blade (1530). Also in some settings, when holding handpiece (1540) using a pencil grip, the user may actuate button (1552) with their index finger and/or may actuate button (1550) with their thumb. As another merely illustrative example, the user may grip handpiece with the broad proximal end (1538) in the palm of their hand, which may allow the user to apply significant controlled force, such as while performing "blunt" work with blade (1530). In some settings, when holding handpiece using this type of grip, the user may actuate either button (1550, 1552) with their finger or thumb.

XVII. Other Exemplary Variations

As will be apparent to those of ordinary skill in the art, the instruments (20, 120, 220, 320, 420, 520, 620, 720, 820, 920, 1020, 1120, 1220, 1320, 1420, 1520) described herein may be subject to numerous types of variations and modifications. Several such modifications will be described in greater detail below, while others will be apparent to those of ordinary skill in the art in view of the teachings herein. While several of the following examples will use only item numbers from FIG. 1, it is for the sake of brevity only, and it should be understood that all of the following examples may be readily applied to the various other types of instruments (120, 220, 320, 420, 520, 620, 720, 820, 920, 1020, 1120, 1220, 1320, 1420, 1520) described herein. Analogousness of components among the various types of instruments (20, 120, 220, 320, 420, 520, 620, 720, 820, 920, 1020, 1120, 1220, 1320, 1420, 1520) will be apparent to those of ordinary skill in the art in view of the teachings herein.

Figure 27:
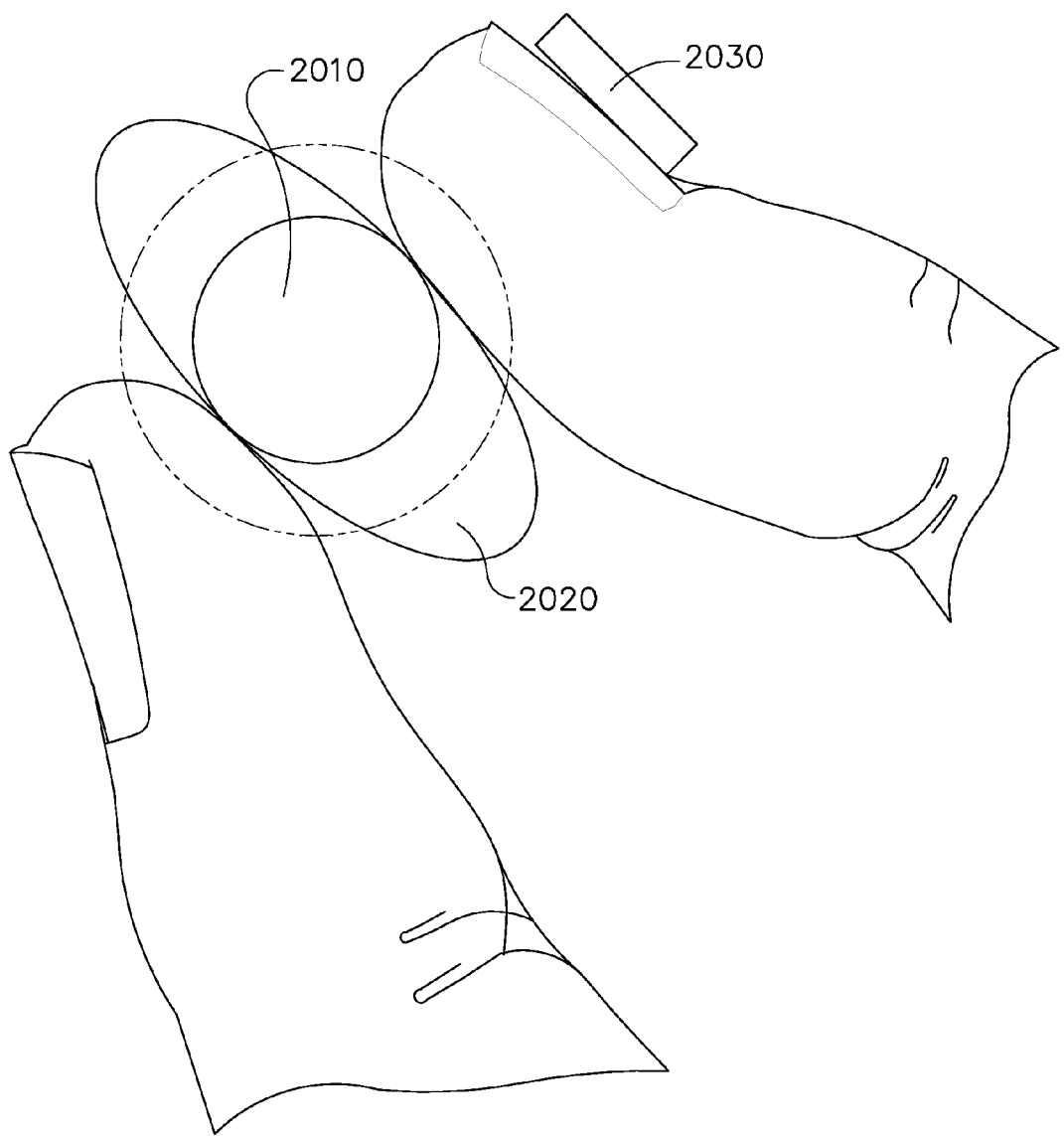
FIG. 27 depicts a cross-sectional end view of another exemplary ultrasonic surgical device, having a flexible shell.

In some versions of instrument (20), and with reference to FIG. 27, handpiece (22) may include a core component (2010) and a flexible outer shell (2020). Flexible outer shell (2020) may be resiliently biased to assume a first configuration, in which shell (2020) does not contact core component (2010). However, shell (2020) may be pinched or squeezed by the user to bring shell (2020) into contact with core component (2010). Instrument (20) may be configured such that shell (2020) must contact core component (2010) in order for blade (24) to be activated. For instance, core component (2010) may include any of the types of switches or "buttons" described herein. This example may thus be analogized to the version of instrument (1120) having a crushable cage (1150) as described above. As another merely illustrative example, core component (2010) may have an electrically conductive portion on its outer surface, while shell (2020) has an electrically conductive portion on its inner surface, such that the two components together form a switch that is closed when the inner surface of shell (2020) contacts the outer surface of core component (2010).

In addition or in the alternative, instrument (20) may be configured to require the user to have a tag (2030) in order to activate blade (24). By way of example only, such a tag (2030) may comprise an RFID tag. Requiring the presence of a tag (2030) within detectable proximity of instrument (20) may, in some instances, reduce the likelihood of inadvertent activation of blade (24). By way of example only, such a tag (2030) may be incorporated into a glove or a thimble-like device for the user to wear.

Figure 28:
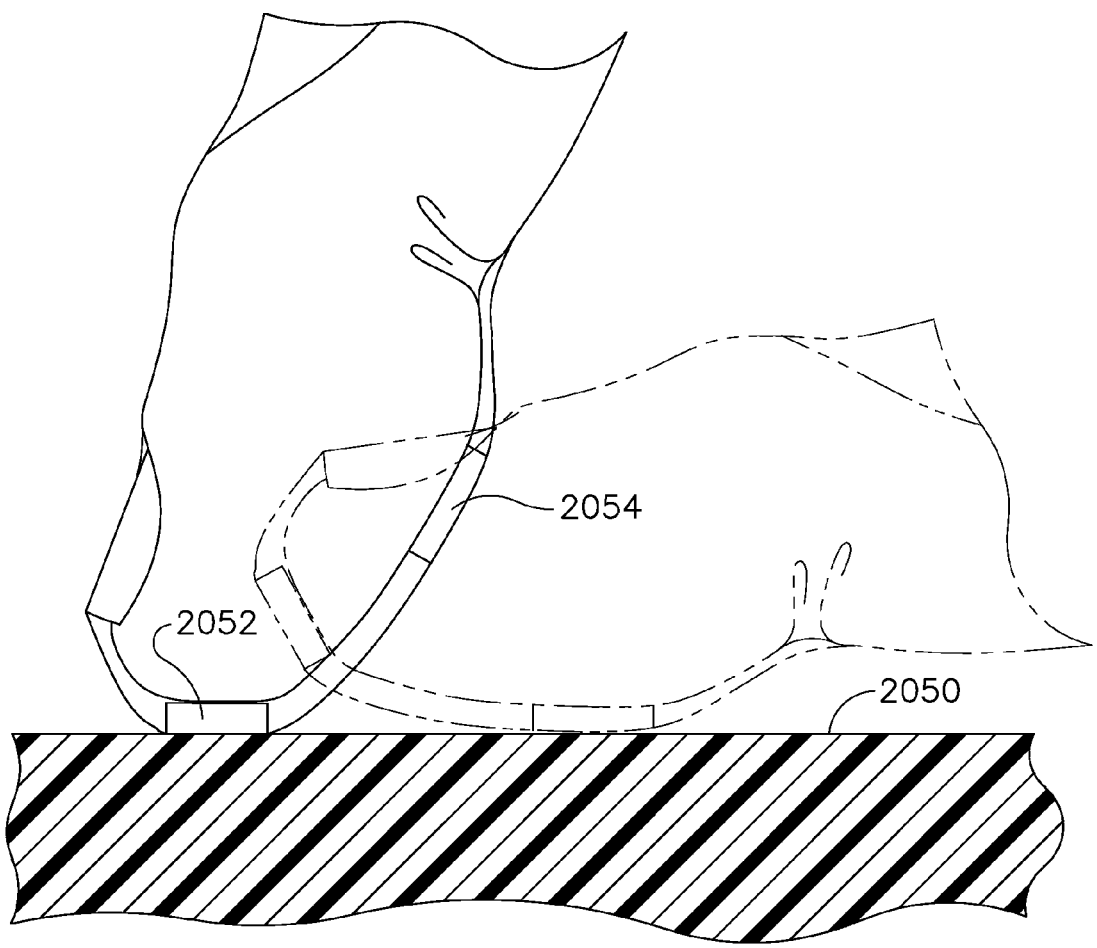
FIG. 28 depicts a side view of exemplary alternative control components of an ultrasonic surgical device.

As another merely illustrative variation, and with reference to FIG. 28, instrument (20) may include an activation surface (2050) that is differentiatingly responsive to sufficient proximity of different tags (2052, 2054). For instance, the user may press a first tag (2052) against activation surface (2050) to activate blade (24) at a "maximum" level of ultrasonic energy; and press a second tag (2054) against activation surface (2050) to activate blade (24) at a "minimum" level of ultrasonic energy. Such tags (2052, 2054) may be incorporated into a glove or a thimble-like device for the user to wear. Various types of tags (2052, 2054) and types of activation surfaces (2050) that may be used to provide such functionality will be apparent to those of ordinary skill in the art in view of the teachings herein.

Figure 29:
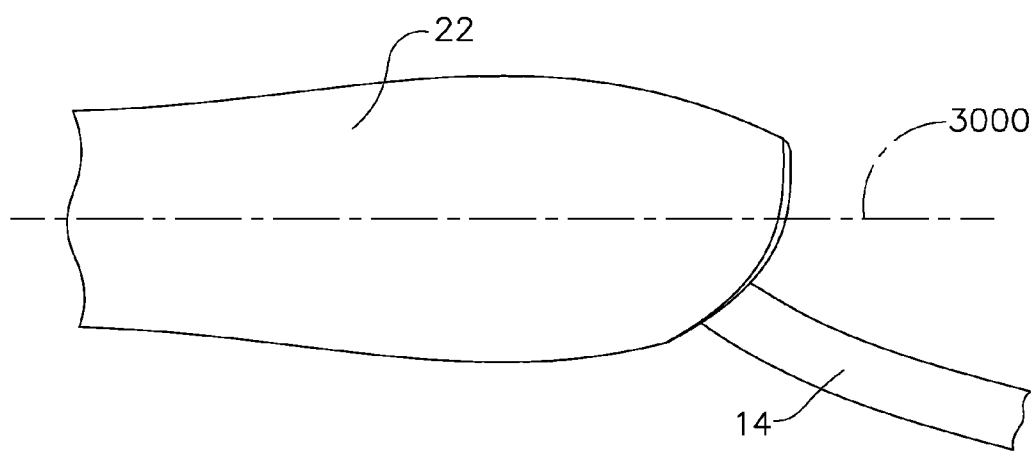
FIG. 29 depicts a partial elevational view of an exemplary proximal end of an ultrasonic surgical device.

As yet another merely illustrative variation, and with reference to FIG. 29, instrument (20) may be configured such that cable (14) exits the proximal end of handpiece (22) at a point that is offset from the longitudinal axis (3000) defined by handpiece (22). This may provide the user with a rotational center of gravity. That is, with cable (14) exiting handpiece (22) slightly eccentric to this longitudinal axis (3000), then handpiece (22) may have a "natural" rotational position, with cable (14) hanging down as shown in FIG. 29. Furthermore, as described above with reference to instrument (820) shown in FIGS. 13-15, cable (14) may rotate independently relative to handpiece (22), which may prevent cable (14) from getting undesirably wrapped up around the user's arm or hand during surgical procedures, such as when the user rotates handpiece (22) about the longitudinal axis defined by handpiece (22).

Instrument (20) may also provide various types of feedback to the user to indicate the operational state of blade (24). For instance, such feedback may simply indicate whether the blade (24) is active or not. Alternatively, such feedback may indicate the energy level being applied to blade (24). The feedback may take a variety of forms, including but not limited to audible feedback, tactile feedback, or visual feedback, including combinations thereof. As one merely illustrative example of visual feedback, instrument (20) may comprise one or more lights (e.g., LED's, etc.). In versions where the energy level being applied to blade (24) is visually indicated, such energy levels may be indicated based on color, pulse train, pulse speed, pulse pattern, or any other use of light. By way of example only, such lighting may be incorporated into control member (852) of instrument (820); into control and activation strip (950) of instrument (920); into control and activation ribs (1350) of instrument (1320); and/or in a variety of other ways. As another merely illustrative example, in versions where the energy level being applied to blade (24) is audibly indicated, such energy levels may be indicated based on timbre, tone, volume, pattern, or any other use of sound. Various other ways in which an instrument (20) may provide feedback to indicate whether blade (24) is active or not and/or the energy level being applied to blade (24) will be apparent to those of ordinary skill in the art in view of the teachings herein. It should also be understood that generator (12) may also provide audible and/or visual feedback indicating the operational status of blade (24), including but not limited to using the types of components and techniques described above with respect to instrument (20). As yet another merely illustrative example, instrument (20) and/or generator (12) may indicate the energy level being applied to blade (24) using numerical and/or graphical representations, and/or in any other suitable fashion.

It should also be understood that the teachings herein are not limited to ultrasonic instruments. By way of example only, various teachings herein (including but not limited to instrument configuration, activation, energy selection, etc.) may be readily incorporated into RF surgical devices such as bi-polar or mono-polar devices, those used for cutting, coagulation, ablation, etc. Various ways in which teachings herein may be applied to RF surgical devices will be apparent to those of ordinary skill in the art. As another merely illustrative example, various teachings herein (including but not limited to instrument configuration, activation, energy selection, etc.) may be readily incorporated into surgical devices that have a mechanically actuated end effector (e.g., mechanically rotating tip, mechanically reciprocating tip, etc.). As yet another merely illustrative example, various teachings herein (including but not limited to instrument configuration, activation, energy selection, etc.) may be readily incorporated into surgical devices that use a laser or some other form of energy to perform a surgical function, therapeutic function, or some other type of function. Various other types of devices to which the teachings herein may be applied will be apparent to those of ordinary skill in the art.

It should be understood that any feature(s), component(s), configuration(s), and/or operability described herein with respect to one particular instrument (20, 120, 220, 320, 420, 520, 620, 720, 820, 920, 1020, 1120, 1220, 1320, 1420, 1520) or other example may readily be incorporated into any other instrument (20, 120, 220, 320, 420, 520, 620, 720, 820, 920, 1020, 1120, 1220, 1320, 1420, 1520) described herein. Therefore, none of the teachings herein should be understood as applying to only one particular version or embodiment of instrument (20, 120, 220, 320, 420, 520, 620, 720, 820, 920, 1020, 1120, 1220, 1320, 1420, 1520) described herein. Every teaching herein is contemplated as being interchangeable among versions and embodiments, such that every teaching herein may be applied to any instrument (20, 120, 220, 320, 420, 520, 620, 720, 820, 920, 1020, 1120, 1220, 1320, 1420, 1520) described herein, in any suitable fashion. Various ways in which the teachings herein may be interchanged among various versions, examples, and embodiments will be apparent to those of ordinary skill in the art in view of the teachings herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An ultrasonic surgical instrument, comprising:
(a) a handpiece having a length;
(b) an ultrasonically actuated blade positioned distal to the handpiece;
(c) a controller operable to select a plurality of ultrasonic energy levels for the blade; and
(d) an activation member operable to activate the blade, wherein the activation member is integral with the handpiece and comprises an external surface having a length, wherein the activation member is positioned and configured to be engaged by a user's hand to selectively activate the blade;

wherein the activation member is accessible from a plurality of positions along the length of the handpiece; and wherein the controller is operable to select an ultrasonic energy level from a virtually infinite number of ultrasonic energy levels for the blade within a predetermined range of ultrasonic energy levels based on a corresponding contact position along the length of the activation member at which a user slidably touches the external surface of the activation member; and wherein the activation member is operable to activate the blade at the selected ultrasonic energy level in response an operator tapping on the activation member.

2. The ultrasonic surgical instrument of claim 1, wherein the activation member comprises an elongate strip running longitudinally along a portion of the length of the handpiece.

3. The ultrasonic surgical instrument of claim 2, wherein the controller is configured to select a first energy level of the blade when a user contacts a distal portion of the strip, wherein the controller is configured to select a second energy level of the blade when a user contacts a proximal portion of the strip, wherein the first energy level is greater than the second energy level.

4. The ultrasonic surgical instrument of claim 1, wherein the activation member comprises a capacitive switch.

5. The ultrasonic surgical instrument of claim 4, wherein the capacitive switch is recessed within the handpiece.

6. The ultrasonic surgical instrument of claim 1, wherein the activation member comprises a strain gauge.

7. A surgical instrument, comprising:
(a) a handpiece;
(b) an end effector positioned distal to the handpiece, wherein the handpiece and end effector are configured to permit a user to apply a force to tissue with the end effector by using the handpiece to force the end effector against the tissue;
(c) a power source in communication with the end effector, wherein the power source is operable to provide a plurality of power levels to the end effector;
(d) a controller, wherein the controller is operable to select one of the power levels provided by the power source to the end effector; and
(e) an activation member, wherein the activation member is integral with the handpiece, wherein the activation member comprises an exterior surface and a longitudinal array of buttons disposed below the exterior surface;

wherein the array of buttons comprises at least three buttons, and wherein the exterior surface is operable to activate each button successively in response to a user sliding a finger across the exterior surface, wherein the controller is operable to progressively and substantially continuously select a series of corresponding predetermined power levels in response to the act of the user sliding a finger across the exterior surface;

wherein each of the buttons of the activation member is configured to activate the end effector at the selected predetermined power level in response to the user tapping the activation member with a predetermined number of taps after the user slides a finger across the exterior surface.

8. The surgical instrument of claim 7, wherein the power source comprises an ultrasonic transducer, wherein the ultrasonic transducer is operable to convert electrical power into ultrasonic vibrational power.

9. An ultrasonic surgical instrument, comprising:
(a) a body having a distal end and a proximal end;
(b) a shaft extending from the distal end of the body;
(c) an ultrasonically actuated blade positioned distal to the body and coupled to the shaft;
(d) means for controlling a level of power provided by a power source to the blade, wherein the means for controlling the level of power comprises an elongate strip having a length, wherein the means for controlling the level of power is configured to select a power level based on a longitudinal position at which an operator stops sliding a finger along the length of the strip; and
(e) means for activating the blade, in response to an operator tapping on the elongate strip, at a power level selected using the means for controlling.

10. The ultrasonic surgical instrument of claim 9, wherein the means for controlling and the means for activating comprise a unitary structure.

* * * * *